Figure 1:
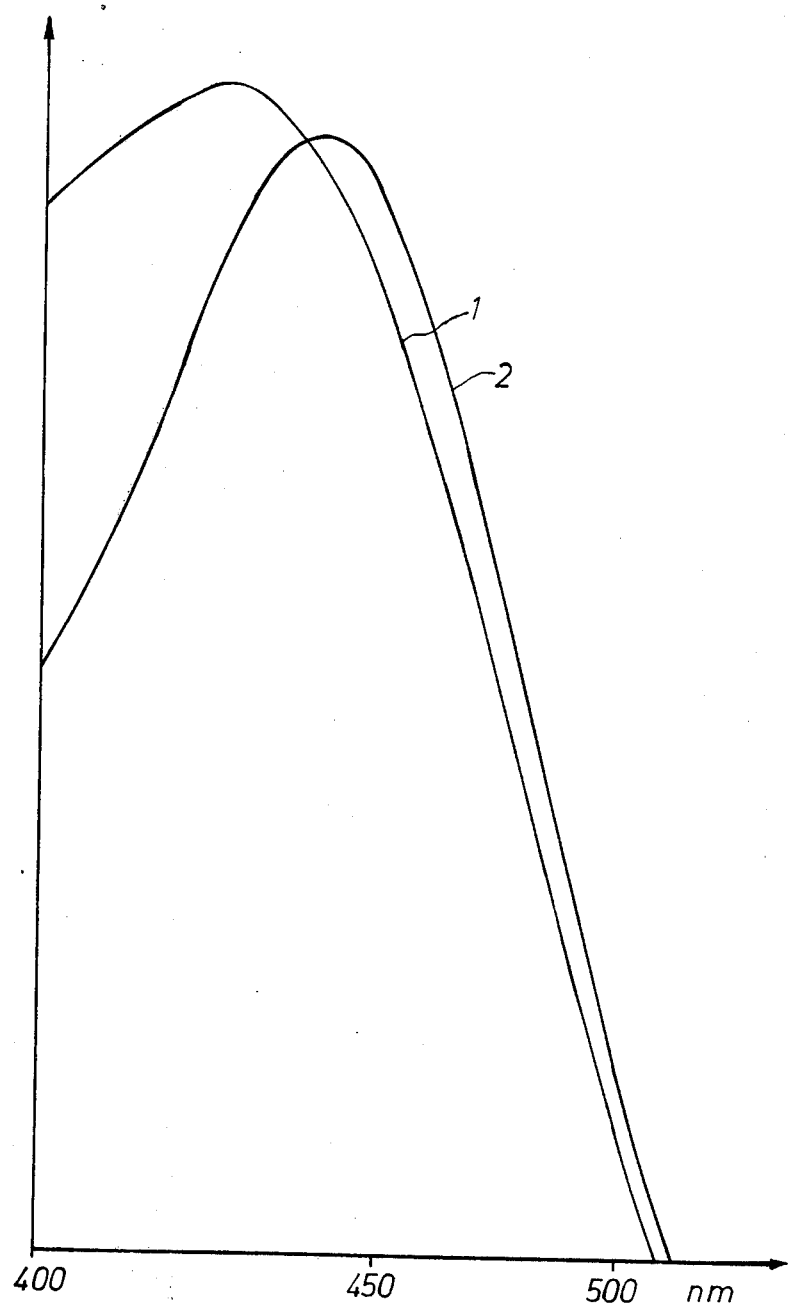

United States Patent [19]

Meier et al.

[11] 4,059,447
[45] Nov. 22, 1977

[54] PHOTOGRAPHIC MATERIAL CONTAINING OXAZOLINONE-2 COUPLERS

[75] Inventors: Ernst Meier, Munich; Hans Heinrich Credner, Hohenschaeftlarn; Wolfgang Lassig, Munich; Karl Küffner, Unterhaching; Karl-Wilhelm Schranz, Odenthal-Hahnenberg, all of Germany

[73] Assignee: AGFA-Gevaert Aktiengesellschaft, Germany

[21] Appl. No.: 643,687

[22] Filed: Dec. 23, 1975

[30] Foreign Application Priority Data

Dec. 31, 1974  Germany .............................. 2461949

[51] Int. Cl.² .......................... G03C 7/00; G03C 1/40
[52] U.S. Cl. .................................. 96/56.4; 96/77; 97/100 R
[58] Field of Search ........................ 96/56.4, 100, 77

[56] References Cited

U.S. PATENT DOCUMENTS

| 2,846,307 | 8/1958 | Woolley | 96/56.4 |
| 3,644,498 | 2/1972 | Loria | 96/100 |

Primary Examiner—David Klein
Assistant Examiner—Richard L. Schilling
Attorney, Agent, or Firm—Connolly and Hutz

[57] ABSTRACT

Monocyclic oxazolinone-2 structures make good 2-equivalent photographic couplers, the oxazolinone-2 ring splitting during the coupling to form a dye. The couplers can be made by condensing an α-halocarbonyl compound with an inorganic cyanate in a substantially aprotic solvent that can contain a small amount of water.

9 Claims, 3 Drawing Figures

PHOTOGRAPHIC MATERIAL CONTAINING OXAZOLINONE-2 COUPLERS

The present invention relates to light-sensitive photographic materials containing coupler compounds with a monocyclic oxazolinone-2-structure and to a process for the production of color photographic images in light-sensitive silver halide materials.

The invention also relates to the oxazolinone-2-couplers as well as their preparation.

It is known to produce colored photographic images by developing the exposed silver halide in a light-sensitive silver halide emulsion layer with an aromatic developer containing a primary amino group in the presence of a color coupler. The color coupler reacts with the oxidized color developer to form a dye image as the silver image is formed.

Subtractive three-color photography is generally carried out using a light-sensitive photographic multilayer material which contains red-sensitive, green-sensitive and blue-sensitive silver halide emulsion layers that give rise to cyan, magenta and yellow dye images respectively when color development is carried out with suitable color couplers.

The coupler used for producing the cyan dye is generally a phenol or naphthol, the coupler for producing the magenta dye is generally a pyrazolone and the coupler for the yellow dye is generally an open-chain ketomethylene compound. The dyes resulting from the coupling reaction are azomethines, indamines or indophenols, depending on the composition of the coupler and of the developer.

Conventional yellow couplers are generally derived from pivaloyl or benzoyl acetanilides containing an active methylene group on which may be substituted a substituent that splits off in the coupling reaction with the oxidized color developer. Couplers without such substitution are so-called 4-equivalent couplers because four equivalents of developable silver halide are required to produce 1 mol of dye in the coupling reaction. Yellow couplers with the foregoing substitution are so-called 2-equivalent couplers and require only two equivalents of developable silver halide to produce 1 mol of dye in the coupling reaction.

Advantages of 2-equivalent couplers compared with 4-equivalent couplers are already known. When 2-equivalent couplers are used, the smaller quantity of silver halide required makes it possible for thinner photographic layers to be used, so that greater resolution and sharpness of the photographic material can be obtained. However the known open-chain substituted or unsubstituted ketomethylene yellow couplers still leave something to be desired in their storage stability. The 2-equivalent couplers, especially those which are more stable in storage, are generally more inert, and on the other hand highly reactive couplers such as, for example α-halogen-β-ketomethylene yellow couplers cause severe fogging. It has therefore already been attempted to increase the storage stability of the photographic materials which contain 2-equivalent couplers by using auxiliary layers, as described in German Offenlegungsschrift No. 2,408,168. However the method described in said Offenlegungsschrift increases the overall thickness of the multilayer photographic material, which is undesirable in modern photograhic materials required to produce images of great sharpness, high resolution and brilliant, saturated colors and developable within relatively short processing times.

There is therefore a demand for a new class of color couplers which are suitable for the production of colored images in light-sensitive silver halide materials and have both a high coupling activity and high stability in storage.

It is among the objects of the present invention to provide a new type of color couplers which are easy to prepare and are suitable for the production of photographic images in color photographic materials.

Additional objects of the present invention include the provision of oxazolinone-2-compounds having a structural coupling moiety to which an oxidation product of a silver halide color developer couples to form a coupling product. The oxazolinone-2-compounds may carry in their 4- or 5-position any substituents which do not interfere with the coupling of the oxazolinone-2-ring with the oxidized color developer and which are themselves not split off during the coupling reaction. The oxazolinone-2-compounds preferably form yellow dyes, when coupled with the color developer.

It is a further object of the present invention to provide a novel method for preparing oxazolinone-2 compounds.

Figure 2:
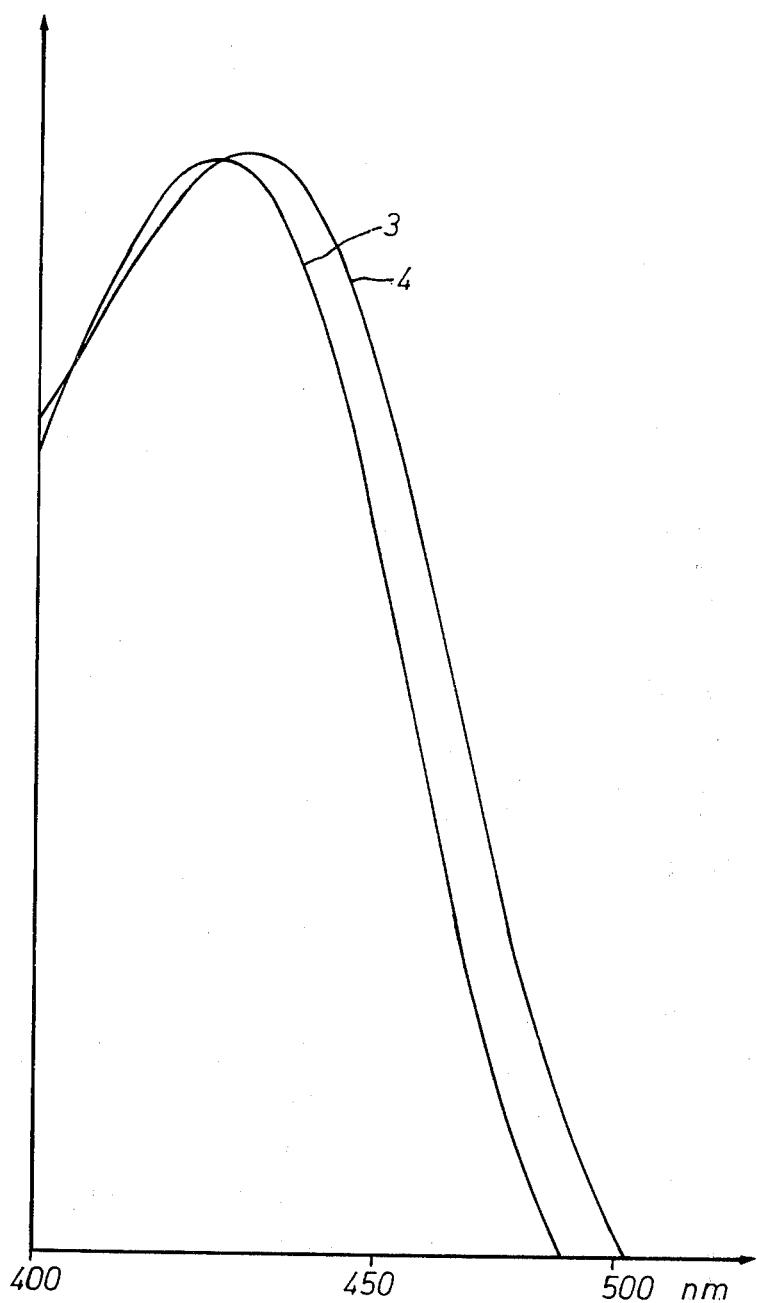
Figure 3:
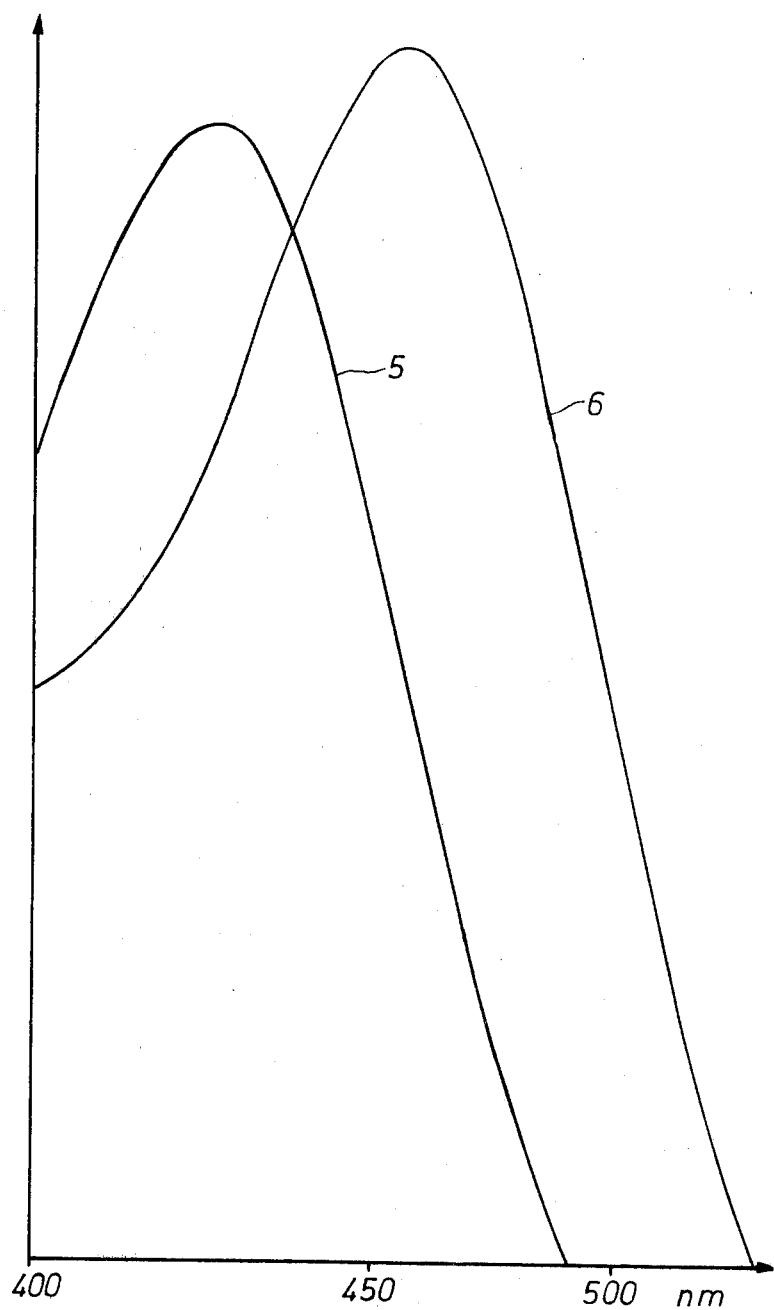

The foregoing as well as additional objects of the present invention are explained in the following description of several of its exemplifications, reference being made to the accompanying drawings, where FIGS. 1, 2 and 3 are light-absorption curves.

The present invention relates to a photographic material that contains a photographic coupler that has a structural coupling moiety to which the oxidation product of a silver halide color developer couples to form a coupling product; according to the present invention the structural coupling moiety is a monocyclic oxazolinone-2-ring, which is substituted at its nitrogen by hydrogen, the

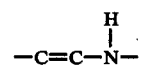

chain structure of the oxazolinone-2 ring may also be present in its tautomeric form

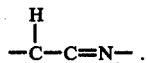

The couplers of the present invention have their oxazolinone-2 ring mono- or disubstituted in its 4- and/or 5-position and preferably have the oxazolinone-2-ring bonded in the 4- or 5-positions to carbons in the remainder of the coupler structure. Such carbons are very desirably part of a hydrocabyl group free of non-aromatic unsaturation, or part of a carbonyl group.

The term "hydrocarbyl" as used in the context of this application is understood to indicate the radical of a hydrocarbon compound including aliphatic, cycloaliphatic, araliphatic and aromatic hydrocarbon compounds. These hydrocarbyl groups may however carry other substituents which are not composed solely of carbon and hydrogen. For example, when the hydrocarbyl group is an alkyl group it may have bonded to it an alkoxy or aroxy substituent or when the hydrocarbyl group is an aryl or aralkyl group it may have bonded to the aryl group thereof one or more substituents such as alkoxy, alkylthio, aroxy, halogen, preferably fluoro or chloro, nitro, amino, acylamino, methylenedioxy, sulfo, sulfamyl or a heterocyclic group.

Examples of oxazolinone-2 compounds which are suitable for the purpose of the present invention are those represented by the following tautomeric formulae:

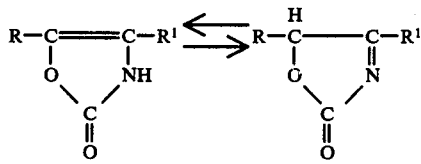

in which
R and R¹, which may be the same or different, represent hydrogen, alkyl, cycloalkyl, aryl, a heterocyclic group or COR² where R² represents hydroxyl, alkoxy, aroxy, alkyl, aryl, a heterocyclic group, or an amino group which may be monosubstituted or disubstituted by alkyl, aryl or heterocyclic groups and, in the case of disubstituted amino group the substituents may constitute the atoms required to complete a 5- or 6-membered heterocyclic ring.

The alkyl and cycloalkyl groups preferably have up to 18 carbons, the aryl groups are preferably phenyl, and the heterocyclic rings preferably have at least 4 carbons, the remaining ring members being N, S or O.

The new coupler compounds are excellently suitable for use in photographic materials and are surprisingly easily obtainable. One very simple method for making them reacts an alpha-halocarbonyl compound with an alkali metal cyanate in a substantially aprotic solvent preferably in the presence of a basic condensing agent.

It is surprisingly found that the halogen in the α-halocarbonyl compound is replaced by the nitrogen of the metal cyanate, and this is immediately followed by a ring closure to form the oxazolinone-2 compounds of the present invention. The ring oxygen of these oxazolinone-2 compounds is directly bonded to the carbon that was the carbonyl carbon of the alpha-halocarbonyl starting compound. This is in contrast to the reactions described by Gompper in Chem. Ber. 89, 1748 (1956), in which an alpha-hydroxy-ketone is reacted with carbamyl compounds or isocyanates to form oxazolinone-2-compounds, in which reaction the ring nitrogen of those oxazolinone-2 rings is directly bonded to the carbon that was the carbonyl carbon of the starting compound.

Coupler compounds suitable for the coupling with oxidized color developer substance can thus be prepared by a single step from simple and inexpensive starting materials. The color couplers according to the invention may be directly incorporated in the silver halide emulsion layers of photographic materials as solutions of diffusion resistant couplers or they may be incorporated in the form of dispersions, with or without the aid so-called oil formers. If the couplers are not diffusion-resistant, they may be dissolved in the color developer and used by the so-called development-in method to effect coupling during development.

The compounds of the monocyclic oxazolinone-2 structure are surprisingly found to constitute a group of exceptionally active coupler compounds. The uncyclized compounds having for example the structure

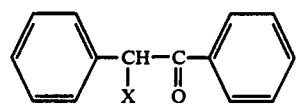

in which X represents hydrogen, halogen or hydroxyl, do not couple or produce dyes with oxidized color developer substances based on p-phenylenediamine because the phenyl group adjacent to the CHX group as second activating group for the substituted methylene group does not sufficiently activate the coupling reaction. When, however, a compound of the foregoing structure is cyclized with an alkali metal cyanate in accordance with the present invention, it gives rise to a 4,5-diphenyl-oxazolinone-2 which readily undergoes a coupling reaction during development with a p-phenylene diamine, to produce a brilliant yellow dye.

The coupling reaction of the oxazolinone-2-structure takes place with oxazolinones-2 which are substituted in 4- and/or 5-position by any substituent which is photographically relatively inert; that is the substituents do not materially detract from the stability, the coupling, and the general processing. Suitable substituents bonded to the oxazolinone-2 ring sufficiently stably so that they are themselves not split off during coupling of the oxazolinone-2 ring. The splitting during the coupling reaction occurs to the oxazolinone-2 ring, whereas the substituents remain attached to the remainder of the oxazolinone-ring on production of the coupling product by reaction with the oxidized color developer. Suitable substituents are attached to the 4- or 5-position or to both positions of the oxazolinone-2 ring by carbon.

Preferred couplers contain in 4- or 5-position substituents attached to the oxazolinone-2 ring by the carbon atom of a

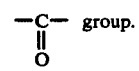 group.

These preferred couplers produce on chromogenic development yellow dyes, some quite bright, the exact color depending on the kind of substituents used.

Particularly suitable oxazolinones-2 of the present invention are those having in 4- or 5-position a

grouping and attached to the 4- or 5-position not carrying said substitution, either hydrogen or a hydrocarbyl group containing up to 40 atoms and free of non-aromatic unsaturation. Open-chained or preferably branched or cyclic alkyls and phenyl are examples of such a group. Aromatic groups such as thienyl are also suitable.

According to the present invention oxazolinone-2 and its above-mentioned derivatives are suitable for use as couplers for photographic silver halide materials. As disclosed above, couplers containing a substituent attached to either the 4- or 5-position of the oxazolinone-2 ring by the carbon of a

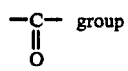  group are generally suitable as yellow couplers. Couplers carrying no such

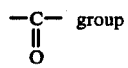  group yield on color-forming coupling dyes that absorb at substantially shorter wave lengths. Such couplers in some cases would be useful as white couplers.

Where R, $R^1$ or $R^2$ in formula I represents or contains alkyl, the alkyl groups are straight or branched chain groups with 1 to 30 carbon atoms, such as methyl, isopropyl, butyl, t-butyl, octyl, dodecyl and hexadecyl, and can be substituted with aryl such as in benzyl or phenylethyl groups.

Where R and/or $R^1$ represents cycloalkyl, it is preferably a 5- or 6-membered cycloalkyl group which may be substituted with alkyl groups, cyclized or uncyclized, and preferably contains 5 to 20 carbon atoms, e.g. cyclohexyl, cyclopentyl or 7,7-dimethylnorobornyl.

Where the groups R, $R^1$ or $R^2$ represent or contain aryl, the aryl groups are preferably naphthyl or phenyl groups, in particular phenyl groups, which may be substituted by one or more substituents, for example by (a) alkyl, alkoxy, alkylamino or alkylthio, the alkyls of which may contain 1 to 20 carbon atoms; (b) acyl or acylamino, the acyls of which may be the acyl portion of alkyl carbonic acid monoesters or monoamides, or of aliphatic or aromatic carboxylic or sulphonic acids, such as heptadecyl carbonamido, dimethylaminosulphonyl, phenyl octadecylamino sulphonyl, methyloctadecylaminocarbonyl, phenylaminocarbonyl or benzoylamino; (c) nitro; (d) halogen such as fluorine, chlorine or bromine; (e) carboxyl; (f) sulpho.

If the groups R, $R^1$ or $R^2$ represent or contain heterocyclic groups, they are most preferably 5- or 6-membered heterocyclic groups, in particular with at least one nitrogen atom, e.g. pyridyl, thiazolyl, oxazolinone-2-yl, quinazolinonyl, morpholino, furanyl or indole groups.

Substitution on the nitrogen of the oxazolinone-2 ring or fusing an aromatic ring on the oxazolinone-2 ring, prevents the specific coupling reaction of the present invention. Such a substitution keeps the carbon atom at the 5-position of the oxazolinone-2 ring from reacting with oxidized color developer to form a coupling product. Benzoxazolone-2 e.g. or N-substituted oxazolinone-2 compounds do not have the possibility to be present in the above-indicated tautomeric

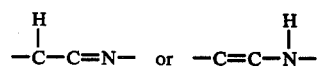

structures of the oxazolinone-2 ring which are vital in the inventive couplers. These similar structures are therefore not capable of a coupling reaction analogous to that of the inventive couplers, and their chemical behaviours are therefore quite different from that of the inventive couplers.

The following are examples of suitable oxazolinone-2 couplers of the present invention:

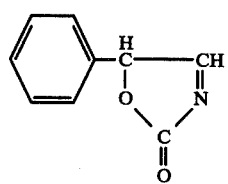

1)

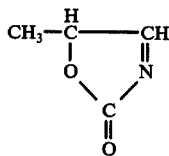

2)

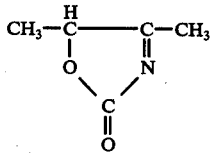

3)

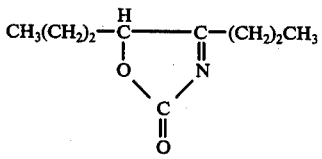

4)

-continued
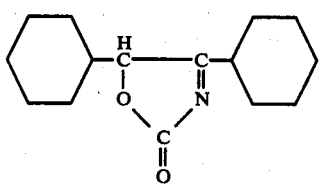
5)
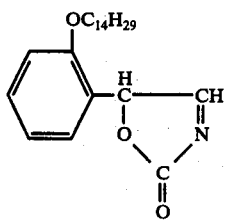
6)
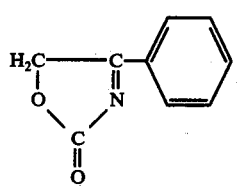
7)
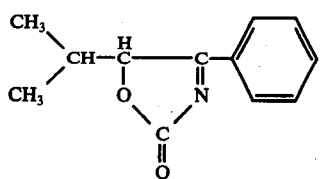
8)
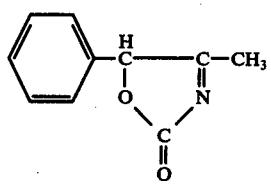
9)
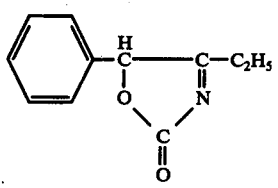
10)
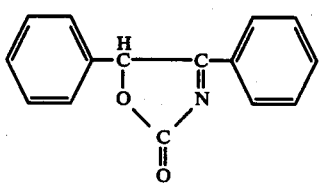
11)
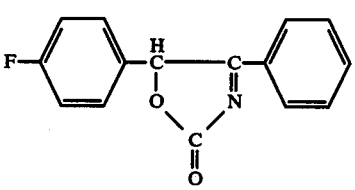
12)

-continued
13)
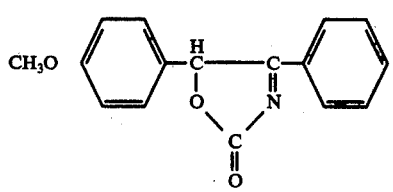
14)
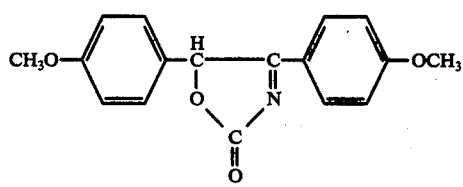
15)
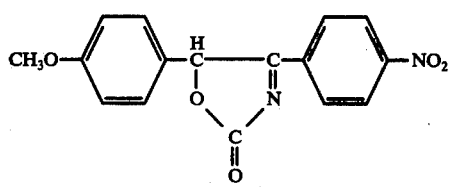
16)
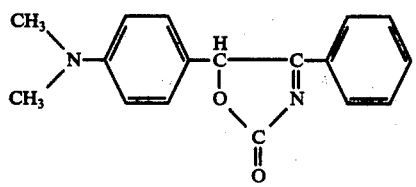
17)
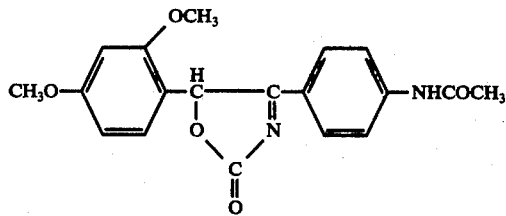
18)
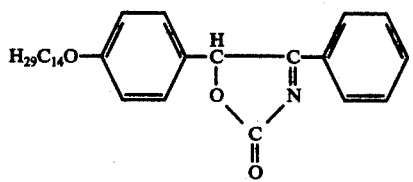
19)
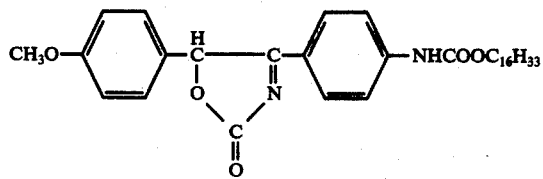
20)
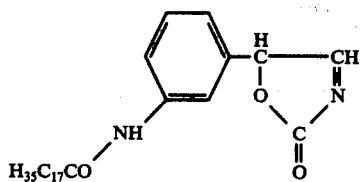

-continued
21)
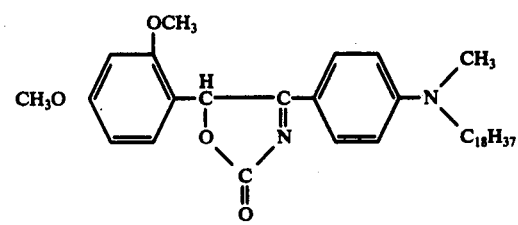
22)
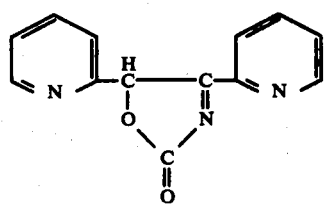
23)
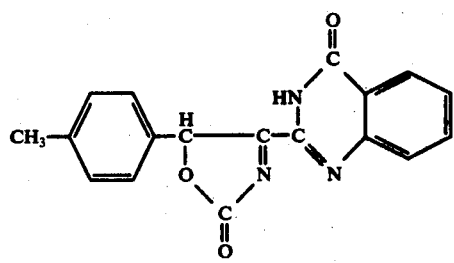
24)
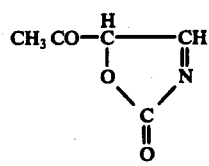
25)
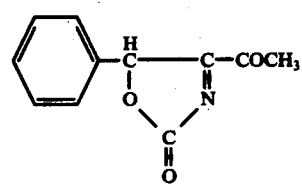
26)
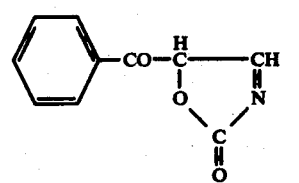
27)
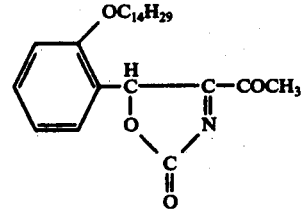
28)
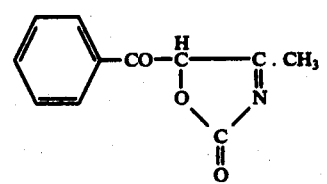

-continued
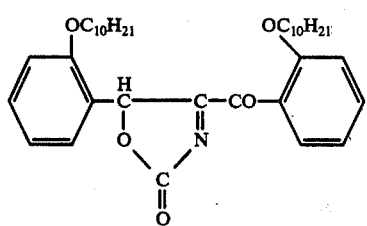 29)
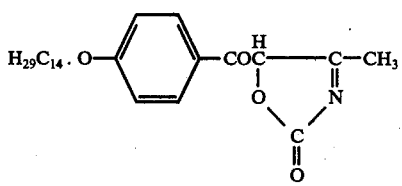 30)
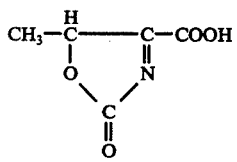 31)
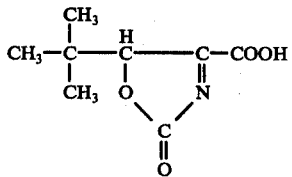 32)
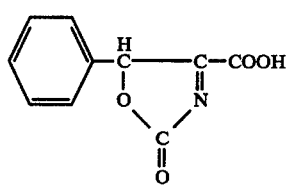 33)
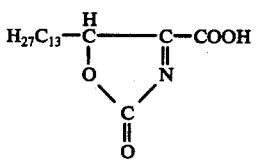 34)
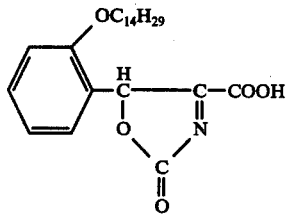 35)
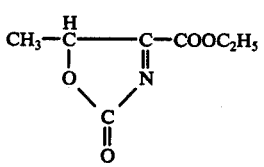 36)
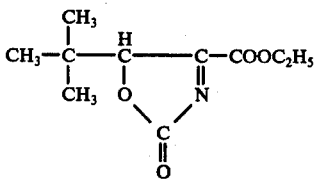 37)

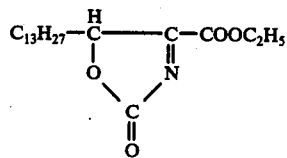 38)
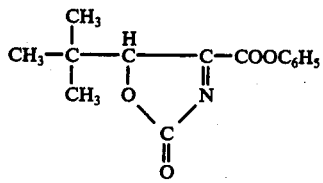 39)
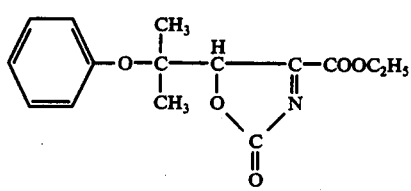 40)
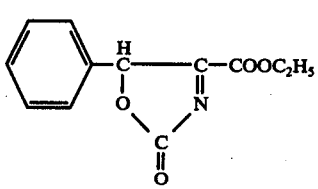 41)
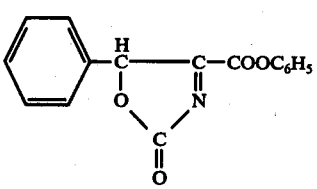 42)
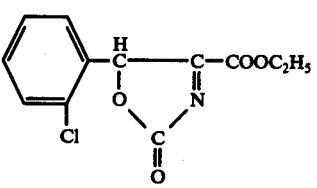 43)
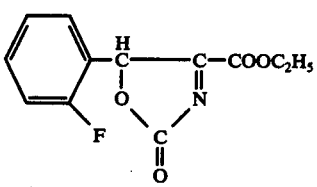 44)
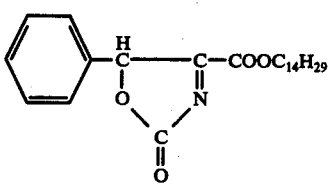 45)
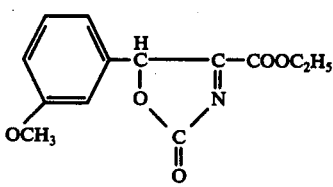 46)

47) 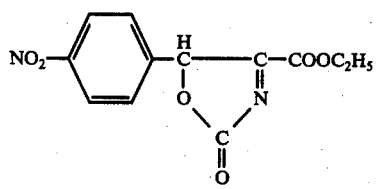
48) 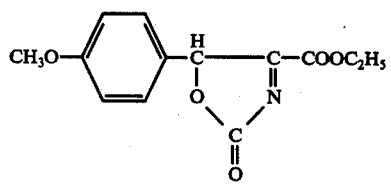
49) 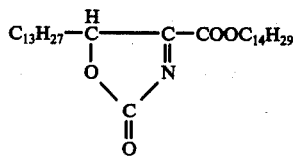
50) 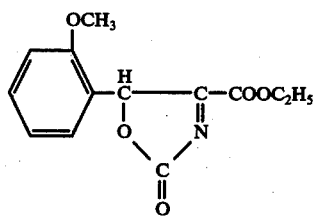
51) 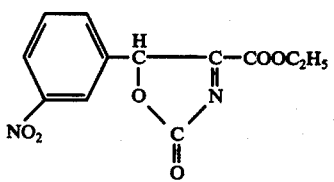
52) 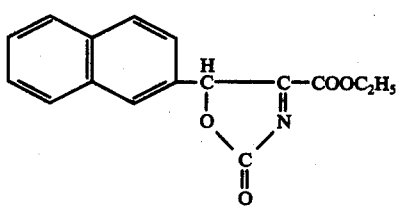
53) 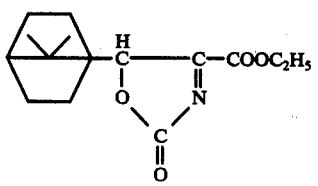
54) 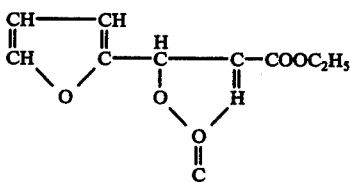

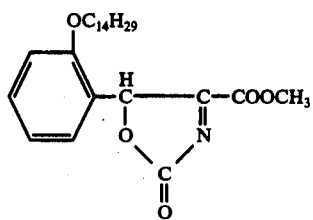
55)
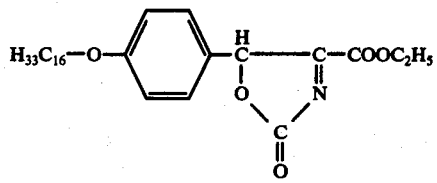
56)
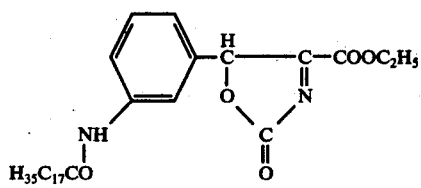
57)
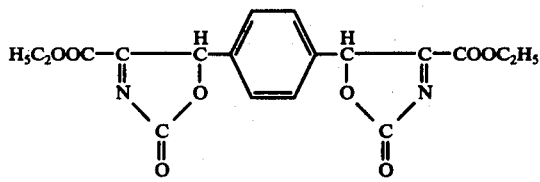
58)
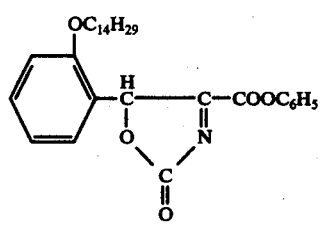
59)
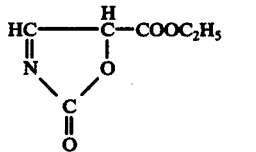
60)
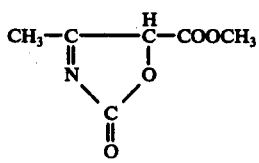
61)
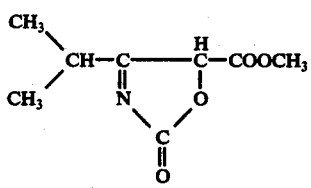
62)
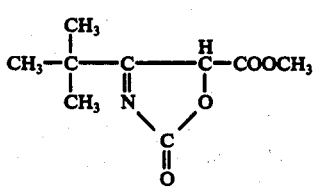
63)

64)
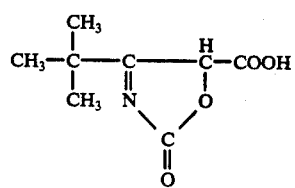
65)
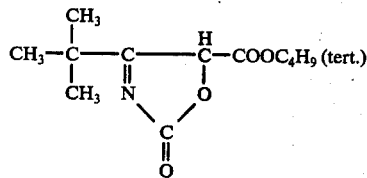
66)
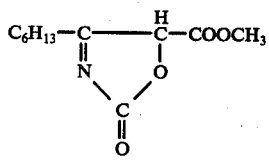
67)
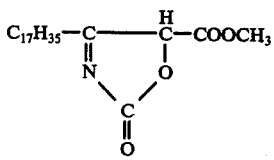
68)
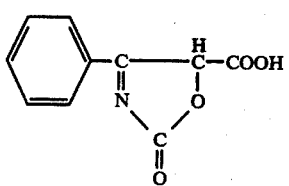
69)
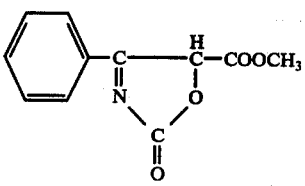
70)
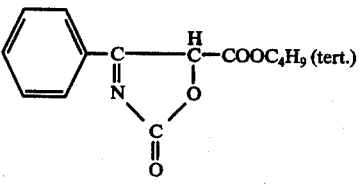
71)
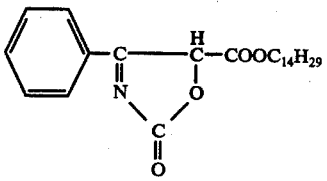
72)
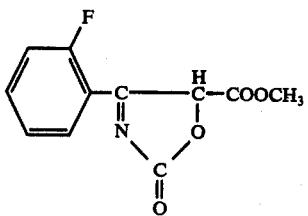

73) 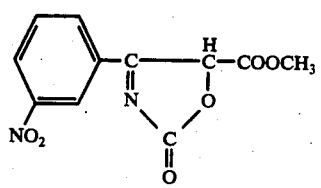
74) 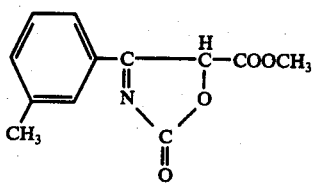
75) 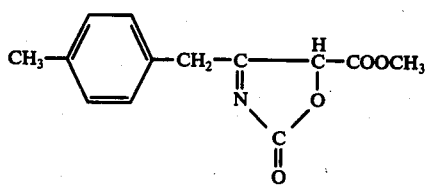
76) 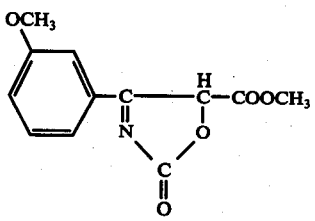
77) 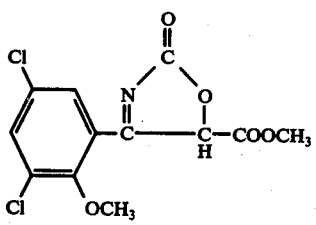
78) 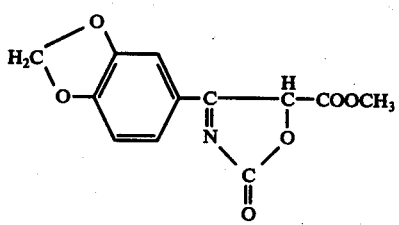
79) 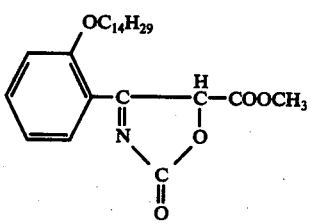
80) 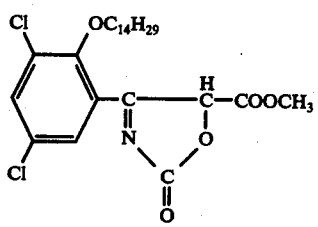

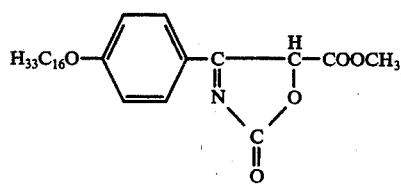 81)
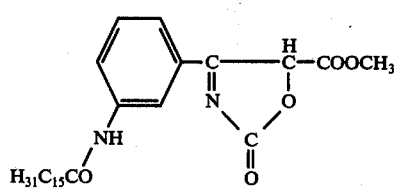 82)
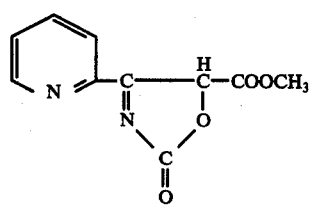 83)
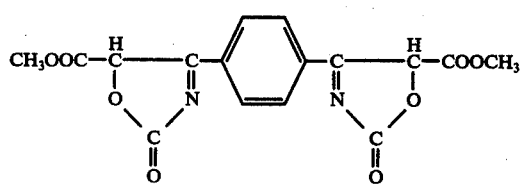 84)
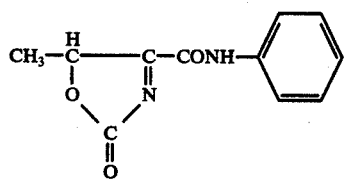 85)
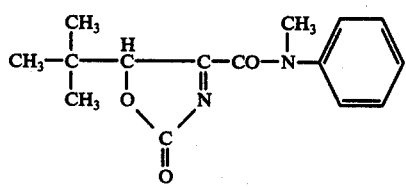 86)
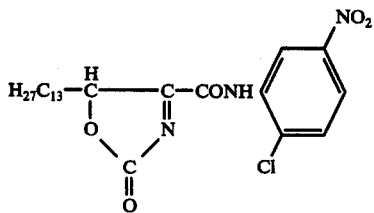 87)
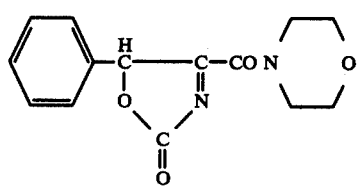 88)

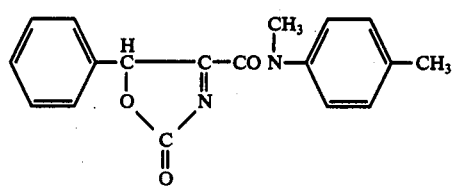
89)
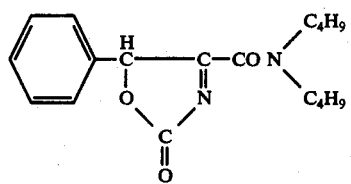
90)
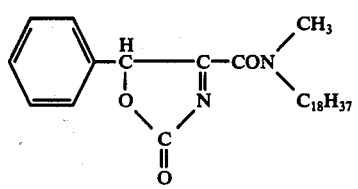
91)
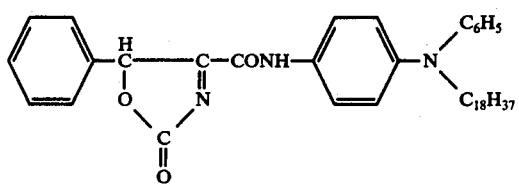
92)
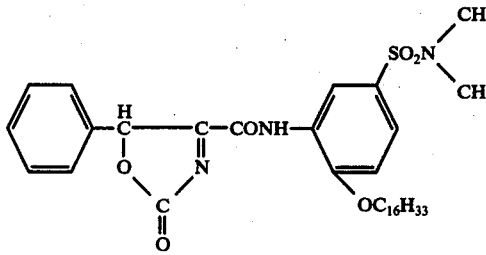
93)
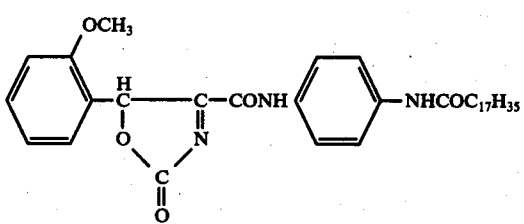
94)
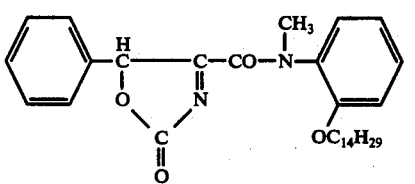
95)
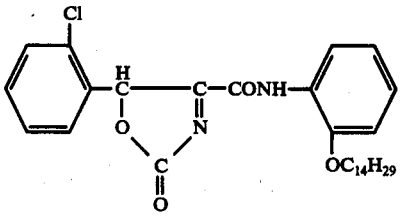
96)

-continued
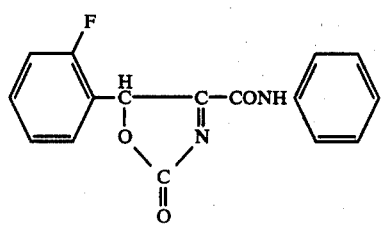
97)
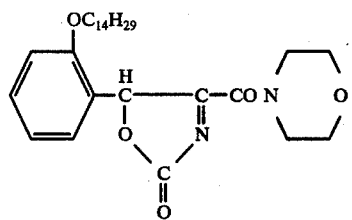
98)
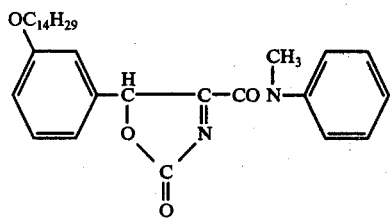
99)
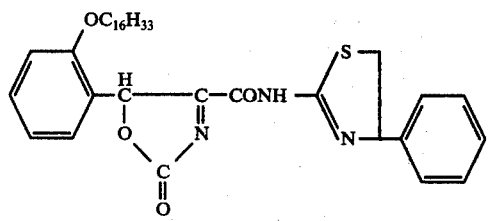
100)
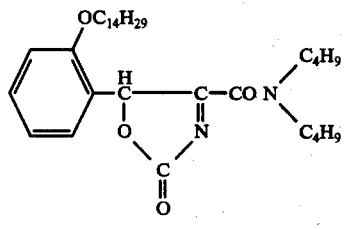
101)
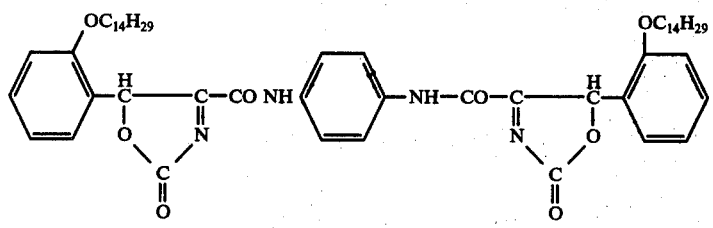
102)
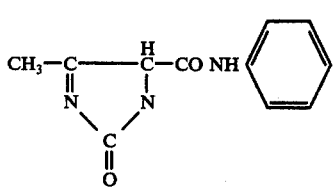
103)
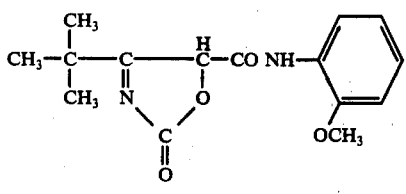
104)

-continued
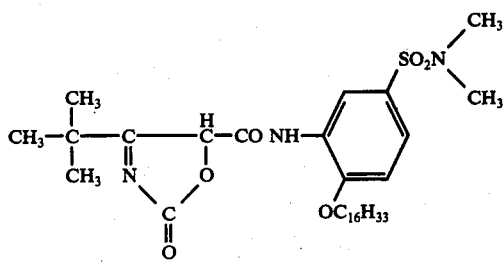
105)
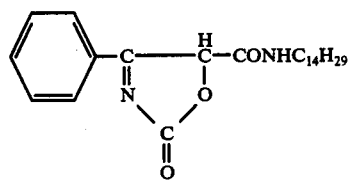
106)
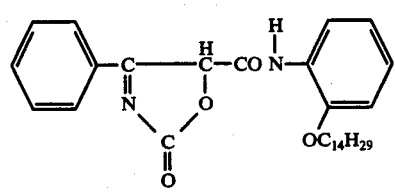
107)
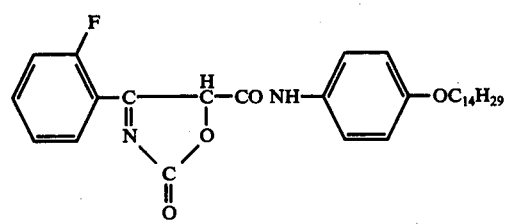
108)
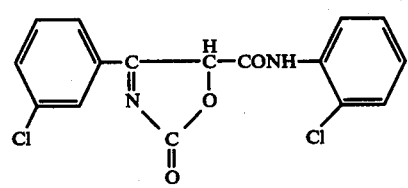
109)
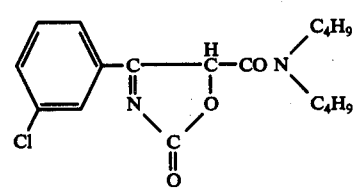
110)
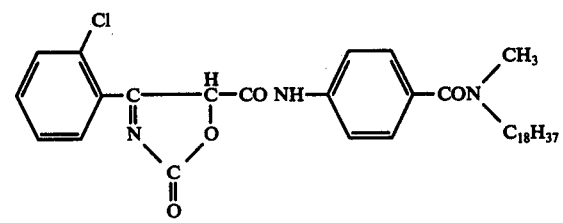
111)
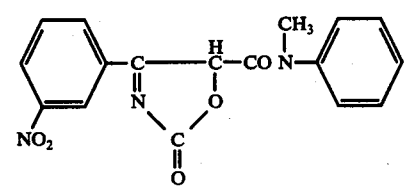
112)

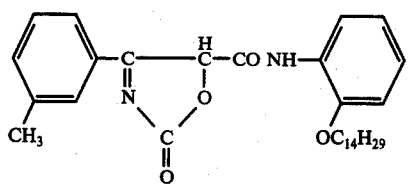
113)
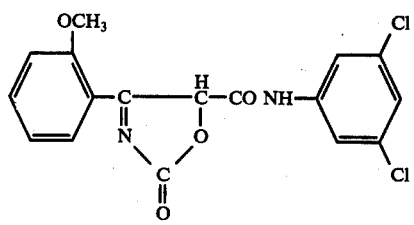
114)
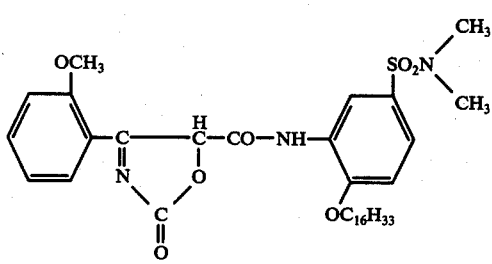
115)
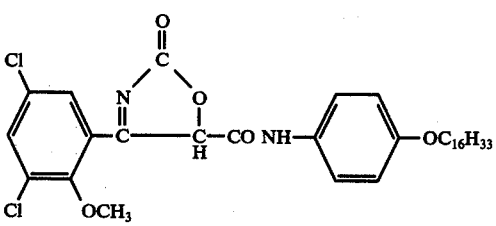
116)
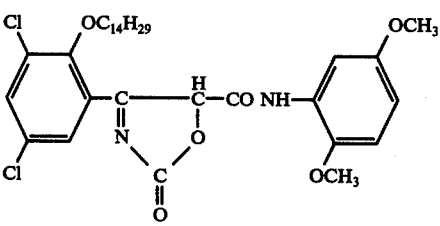
117)
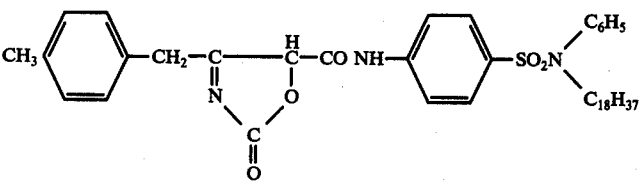
118)
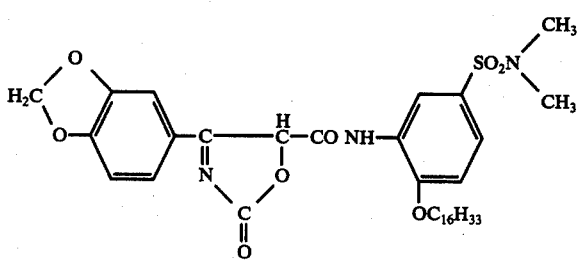
119)

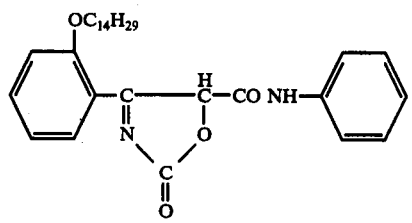
120)
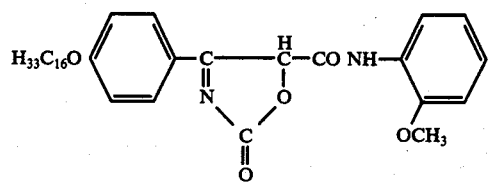
121)
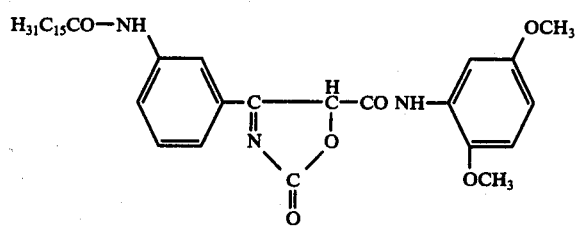
122)
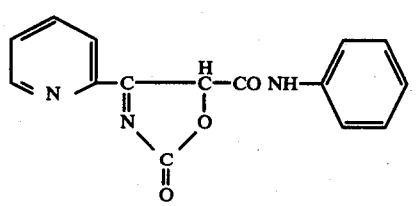
123)
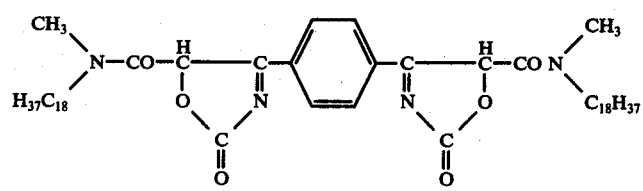
124)
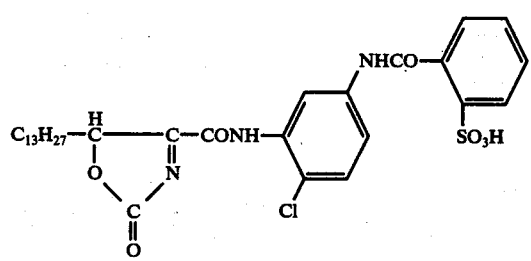
125)
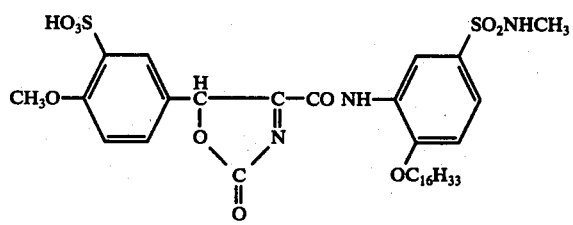
126)
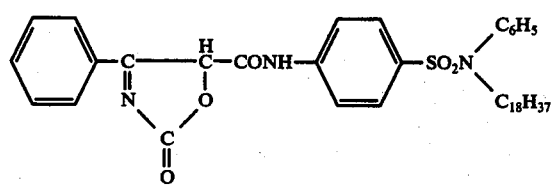
127)

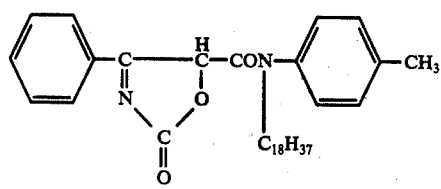
128)
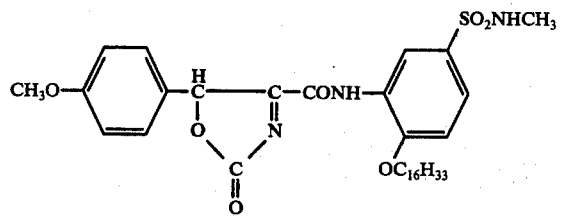
129)
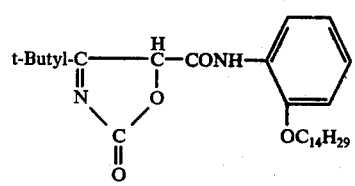
130)
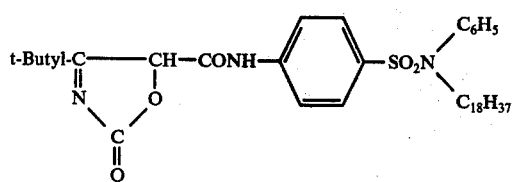
131)
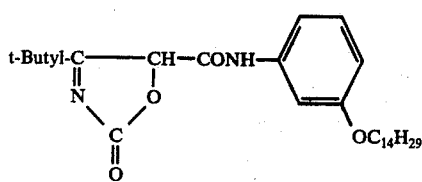
132)
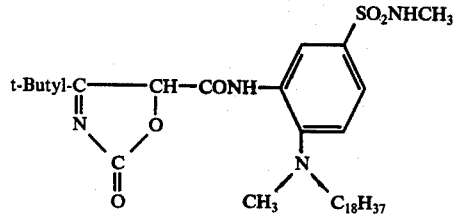
133)
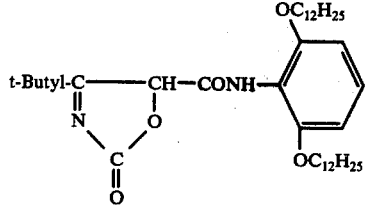
134)
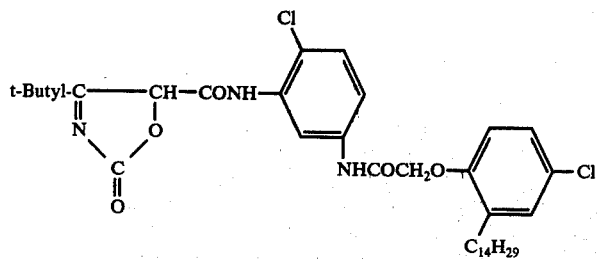
135)

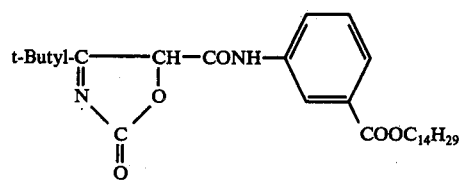
136)

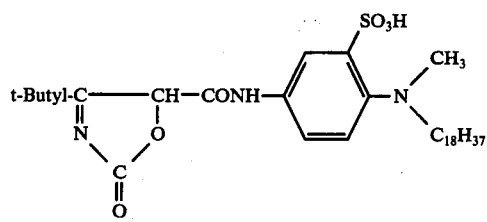
137)

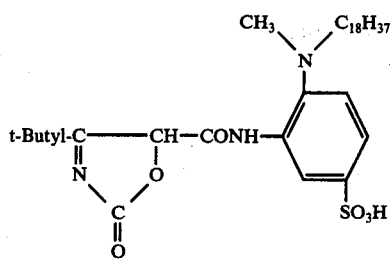
138)

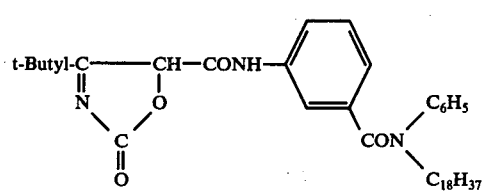
139)

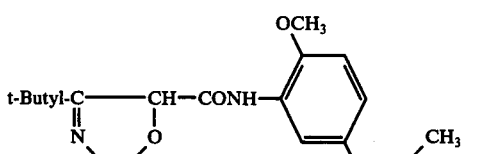
140)

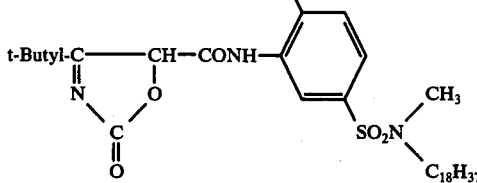
141)

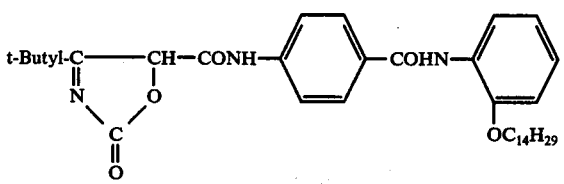

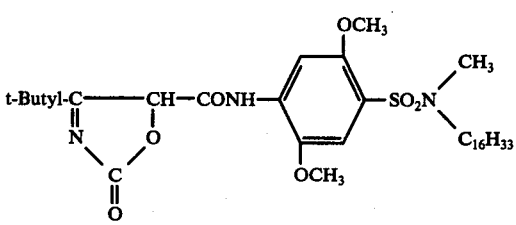
142)

In the compounds of the above formula I, R and $R^1$ are preferably different from each other.

Where the coupler compounds used according to the invention carry no long-chain aliphatic substituents, they are preferably used in developer solutions as couplers which are not diffusion resistant. Couplers of this kind include, for example, those specified under the numbers 26, 28, 88-90, 97, 103, 104, 109, 110, 114 and 123.

Those examples of couplers which can be incorporated as diffusion-resistant couplers contain at least one radical which confers diffusion resistance on them. By radicals which confer diffusion resistance are meant radicals which make it possible for the compounds according to the present invention to be incorporated in a diffusion-fast form in the hydrophilic colloids normally used in photographic materials. Particularly suitable radicals for this purpose are organic radicals which generally contain straight or branched chain aliphatic groups and may also contain isocyclic or heterocyclic aromatic groups. The aliphatic part of these radicals generally contains 8 to 20 carbon atoms. The radicals are attached to the remainder of the molecule either directly or indirectly, for example through one of the following groups: —CONH—, —SO$_2$NH—, —CO—, —SO$_2$—, —O—, —S—, or —NR$^3$— in which R$^3$ represents hydrogen or alkyl.

The radical which confers diffusion resistance may in addition contain water-solubilizing groups, e.g. sulpho groups or carboxyl groups, and these may also be present in an anionic form. Since the diffusion properties depend on the molecular size of the whole compound, it is sufficient in some cases, for example, if the whole molecule is large enough, to use short chain radicals for conferring diffusion resistance, for example one or more tertiary butyl, cycloalkyl or isoamyl radicals.

Examples of couplers which can be incorporated as diffusion resistant couplers in the hydrophilic colloid layer of a light-sensitive photographic material are: Couplers 6, 19 to 21, 27, 29, 30, 45, 49, 55 to 57, 59, 71, 79 to 82, 91 to 96, 98 to 102, 105 to 108, etc.

Preferred couplers of the present invention have a carbonyl bonded to their 4- or 5-position as in the following formulae II or III or their tautomeric forms:

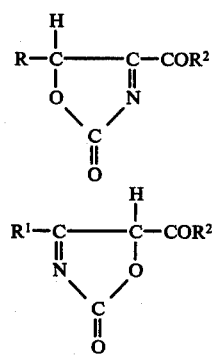

in which
R and R$^1$ represent (a) hydrogen or, in particular, (b) a straight, branched chain or cyclic alkyl group with 1 to 30, preferably up to 20 carbon atoms, which may be substituted by alkoxy with up to 20 carbons, phenoxy or phenyl, (for example a methyl, isopropyl, α-phenoxyisopropyl, t-butyl, n-octadecyl, cyclopentyl, cyclohexyl or norbornyl group); (c) an aryl group such as a phenyl or naphthyl group, in particular a phenyl group which is substituted by one or more substituents, for example by an alkyl group containing 1 to 20 carbon atoms, an alkoxy group containing 1 to 20 carbon atoms, an alkylthio group containing 1 to 20 carbon atoms, an amino group or a sulphamyl or carbamyl group, in which amino, sulphamyl or carbamyl groups one or both hydrogen atoms may be substituted by the same or different alkyl or aryl of the kinds listed above, or heterocyclic groups as listed below; (d) an acyl or acylamino group, the acyls of which may be acyl portions of alkyl carbonic monoesters or aliphatic or aromatic carboxylic or sulphonic acids; (e) a carboxyl group; or (f) a heterocyclic group such as a 5- or 5-membered saturated or partly saturated heterocyclic ring in which at least four of the ring members are carbon and the remaining ring members are N, S, or O. Preferred heterocyclic rings contain at least one nitrogen, oxygen or sulfur atom, for example thienyl, pyridinyl, furanyl group or morpholine; and R$^2$ represents (a) hydroxyl, (b) alkoxy with 1 to 30, preferably 8 to 20 carbon atoms; (c) aryl, in particular phenyl, if desired substituted with one or more of the substituents indicated under R and R$^1$ for the phenyl group, or preferably (d) the group

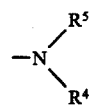

in which R$^4$ and R$^5$ which may be the same or different, represent (a) hydrogen, (b) alkyl in particular with 1 to 30, most preferably up to 20 carbon atoms such as methyl, ethyl or octadecyl, (c) aryl such as naphthyl or phenyl, in particular phenyl, which may be substituted preferably in m- or p-position by one or more of the substituents given under R and R$^1$ for the phenyl group, or R$^4$ and R$^5$ either individually or together may represent or form a heterocyclic group such as 5- or 6-membered saturated or partly saturated heterocyclic ring such as a piperidinyl or morpholine group, in which at least four ring members are carbon and the remaining ring members are N, S or O.

Some of the couplers which may be used according to the present invention are known compounds and can be prepared by the methods described in the literature. Thus 4,5-Di-pyridyl-(2')-oxazolinone-(2) can be prepared by the method described by Cramer and Krum in Chem. Ber. 86, 1588 (1953).

Oxazolinone-2 compounds substituted by alkyl, aryl or heterocyclic groups in the 4- and 5-position can be prepared by reacting α-hydroxyketones with ethylcarbamate or carbamic acid chloride by the method described in the above-cited 1956 publication.

The reaction of α-aminoketones with phosgene by the methods described by de Stevens in J. Org. Chem. 23, 1572, provides only moderate yields of oxazolinones substituted in the 4- and 5-position.

The methods described by Huisgen and Blaschke in Chem. Ber. 98, 2985 (1965) would also appear to be of only limited applicability for the preparation of the oxazolinones of the present invention because the α-aminoketone compounds required for these methods are too difficult to obtain.

As already mentioned above, oxazolinone-2 compounds of the present invention can easily be obtained by the reaction of α-halocarbonyl compounds with alkali metal cyanate in accordance with the present invention, as described in detail below. For instance one type of such α-halocarbonyl compounds corresponds to formula IV (for which tautomeric forms are given):

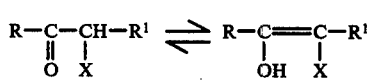

in which
R and R$^1$ have the meanings specified under formula I, and X represents a halogen such as chlorine or bromine. This compound is mixed with an alkali metal cyanate such as sodium or potassium cyanate in the presence of an aprotic, preferably polar solvent at a reaction temperature of 20 to 150° C, if desired with the addition of a small quantity of water.

Suitable aprotic solvents are hydrocarbyl ethers having up to 10 carbon atoms, lower dialkyl sulphoxides, hydrocarbyl cyanides having up to 10 carbons, acid amides having less than 10 carbons and in which each acid group is amidated and each amido group is fully alkylated with lower alkyls, and mixtures thereof. Preferred are carboxylic acid amides, phosphonic and phosphoric acid amides such as hexamethylphosphoric acid triamide and dimethylformamide, dimethylsulphoxide and acetonitrile. The lower alkyls in said solvents have up to 5 carbons.

The following method is preferably employed:

1 Mol of a compound of the general formula IV is dissolved in a 5- to 10-times excess of acetonitrile and the solution thus formed added dropwise with stirring at a bath temperature of 90 to 100° C to a suspension of 3 to 5 mol of alkali metal cyanate, preferably sodium cyanate, in 2 to 5 times its quantity of hexamethyl phosphoric acid triamide, dimethyl formamide or dimethyl sulphoxide to which optionally 0.01 to 1% of water based on the aprotic solvent used has previously been added. The addition of water improves the solubility of sodium cyanate, and improves in some instances the yield.

On the other hand if more water is used it is possible that side reactions may occur, for example the α-halogen is partly hydrolized instead of reacting with the alkalicyanate in the desired manner.

After a further 10 to 160 minutes, the reaction mixture may be taken up in a solvent such as ethyl acetate or methylene chloride, and unreacted alkali metal cyanate is filtered off. The resulting solution is then neutralized with glacial acetic acid and extracted by shaking several times with water, or with aqueous sodium chloride if the oxazolinone compound is too soluble in water. The organic phase has its solvent evaporated off and the residue thus left is recrystallized for a suitable solvent. The yields obtained are between about 20 and 80% of theory, depending on the starting compound used.

The following are examples of α-halocarbonyl compounds of the general formula IV which are converted in this way into oxazolinone-2 compounds of the general formula I:

chloracetone;
2-chloro-butanone-(3);
chloromethyl-isopropylketone;
4-chloro-octanone-(5);
α-chloro-acetophenone;
α-chloro-propiophenone;
α-chloro-butyrophenone;
α-chloro-phenylacetaldehyde;
desyl chloride;
1-chloro-2-oxo-1,2-dicyclohexyl-ethane;
α-chloro-benzyl-(4-fluorophenyl)-ketone;
(α-chloro-4-methoxybenzyl)-(4-methoxyphenyl)-ketone;
(α-chloro-4-nitrobenzyl)-(4-methoxyphenyl)-ketone;
α-chloro-benzyl-(4-N,N-dimethylaminophenyl)-ketone;
1-chloro-2-oxo-1,2-di-α-pyridyl-ethane;
1-chloro-2-oxo-1-quinazolinonyl-(2)-2-p-tolyl-ethane;
(α-chloro-4-acetaminobenzyl)-(2,4-dimethoxyphenyl)-ketone;
α-chloro-benzyl-(4-tetradecyloxyphenyl)-ketone;
(α-chloro-4-cetyloxycarbamidobenzyl)-(4-methoxyphenyl)-ketone;
chloromethyl-(3-stearoylaminophenyl)-ketone;
(α-chloro-4-N-methyl-N-octadecylaminobenzyl)-(2,4-dimethoxyphenyl)-ketone;
2-chloro-1,3-dioxo-1-phenyl-butane;
3-bromo-1,2-dioxo-1-phenyl-propane;
3-bromo-1,2-dioxo-1-phenyl-butane;
1-chloro-2,3-dioxo-butane;
3-chloro-1,2-dioxo-1-p-tetradecyloxyphenyl-butane;
2-chloro-1,3-dioxo-1,3-di-(o-decyloxyphenyl)-propane;
2-chloro-1,3-dioxo-1-(o-tetradecyloxyphenyl)-butane;
α-chloro-acetic acid ethyl ester;
α-chloro-pivaloyl acetic acid ethyl ester;
α-chloro-myristoyl acetic acid ethyl ester;
α-chloro-benzoylacetic acid ethyl ester;
α-chloro-o-chlorobenzoyl acetic acid ethyl ester;
α-chloro-p-chlorobenzoylacetic acid ethyl ester;
α-chloro-o-fluorobenzoylacetic acid ethyl ester;
α-chloro-benzoylacetic acid phenyl ester;
α-chloro-m-nitrobenzoylacetic acid ethyl ester;
α-chloro-p-nitrobenzoylacetic acid ethyl ester;
α-chloro-o-methoxybenzoylacetic acid ethyl ester;
α-chloro-m-methoxybenzoylacetic acid ethyl ester;
α-chloro-p-methoxybenzoylacetic acid ethyl ester;
α-chloro-2,5-dimethoxybenzoylacetic acid ethyl ester;
α-chloro-2-phenoxy-propionyl-(2)-acetic acid ethyl ester;
α-chloro-thienyl-2-oyl-acetic acid ethyl ester;
α-chloro-furyl-2-acetic acid ethyl ester;
α-chloro-naphthyl-2-oyl-acetic acid ethyl ester;
α-chloro-bornyl-2-oyl-acetic acid ethyl ester;
α-chloro-o-tetradecyloxy-benzoylacetic acid methyl ester;
α-chloro-o-tetradecyloxy-benzoylacetic phenyl ester;
α-chloro-p-tetradecyloxybenzoylacetic acid ethyl ester;
α-chloro-p-cetyloxybenzoylacetic acid phenyl ester;
phenylene-1,4-bis-(α-chloro-β-oxo-propionic acid ethyl ester;
bromopyruvic acid ethyl ester;
3-chloro-2-oxo-butyric acid methyl ester;
3-chloro-2-oxo-4-methyl-pentanoic acid ethyl ester;
3-chloro-2-oxo-4,4-dimethyl-pentanoic acid methyl ester;
3-chloro-2-oxo-4,4-dimethyl-pentanoic acid-t-butyl ester;
3-chloro-2-oxo-nonanoic acid methyl ester;
3-chloro-2-oxo-eicosanoic acid methyl ester;
3-chloro-2-oxo-3-phenyl-propionic acid methyl ester;
3-chloro-2-oxo-3-phenyl-propionic acid-t-butyl ester;
3-chloro-2-oxo-3-o-chlorophenyl-propionic acid methyl ester;
3-chloro-2-oxo-3-m-chlorophenyl-propionic acid methyl ester;
3-chloro-2-oxo-3-o-fluorophenyl-propionic acid methyl ester;
3-chloro-2-oxo-3-m-nitrophenyl-propionic acid methyl ester;
3-chloro-2-oxo-3-m-tolyl-propionic acid methyl ester;
3-chloro-2-oxo-3-o-methoxyphenyl-propionic acid methyl ester;
3-chloro-2-oxo-3-o-methoxyphenyl-propionic acid t-butyl ester;
3-chloro-2-oxo-4-p-tolyl-butyric acid methyl ester;

3-chloro-2-oxo-3-(3,5-dichloro-2-methoxyphenyl)-propionic acid methyl ester;
3-chloro-2-oxo-3-(3,5-dichloro-2-tetradecyloxyphenyl)-propionic acid methyl ester;
3-chloro-2-oxo-3-(3,4-methylenedioxyphenyl)-propionic acid methyl ester;
3-chloro-2-oxo-3-o-tetradecyloxyphenyl-propionic acid methyl ester;
3-chloro-2-oxo-3-o-tetradecyloxyphenyl-propionic acid t-butyl ester;
3-chloro-2-oxo-3-p-cetyloxyphenyl-propionic acid methyl ester;
3-chloro-2-oxo-3-m-palmitoylamidophenyl-propionic acid methyl ester;
3-chloro-2-oxo-3-p-carbethoxyphenyl-propionic acid methyl ester;
3-chloro-2-oxo-3-pyridyl-(2)-propionic acid methyl ester;
phenylene-1,3-bis-($\beta$-chloro-$\alpha$-oxo-propionic acid methyl ester;
$\alpha$-chloro-acetyl-acetanilide;
$\alpha$-chloro-pivaloyl-aceto-N-methylanilide;
$\alpha$-chloro-myristoyl-aceto-(2-chloro-5-nitroanilide);
$\alpha$-chloro-benzoyl-aceto-morpholide;
$\alpha$-chloro-benzoyl-aceto-N-methyl-p-toluidide;
$\alpha$-chloro-benzoyl-aceto-N,N-dibutylamide;
$\alpha$-chloro-o-methoxybenzoyl-acetanilide;
$\alpha$-chloro-o-chlorobenzoyl-aceto-o-tetradecyloxyanilide;
$\alpha$-chloro-o-methoxybenzoyl-aceto-N-methyl-o-tetradecyloxyanilide;
$\alpha$-chloro-benzoyl-aceto-N-methyl-N-octadecylanilide;
$\alpha$-chloro-o-fluorobenzoyl-acetanilide;
$\alpha$-chloro-o-tetradecyloxybenzoyl-acetomorpholide;
$\alpha$-chloro-o-tetradecyloxybenzoyl-aceto-N-methylanilide;
$\alpha$-chloro-o-terradecyloxybenzoyl-aceto-o-methoxyanilide;
$\alpha$-chloro-o-tetradecyloxybenzoyl-aceto-N,N-dibutylamide;
$\alpha$-chloro-benzoyl-aceto-(4-N-phenyl-N-octadecylsulphamylanilide);
$\alpha$-chloro-benzoyl-aceto-(2-ocetyloxy-5-N,N-dimethylsulphamylanilide) and
bis-($\alpha$-chloro-o-tetradecyloxybenzoyl-aceto)-1,4-phenylenediamide.

Other conventional $\alpha$-halo-$\beta$-ketomethylene yellow coupler compounds may, of course, also be converted into the couplers according to the invention. Examples of suitable $\alpha$-halo-$\beta$-ketomethylene yellow coupler compounds have been described in U.S. Pat. Specifications No. 2,728,658; No. 3,265,508; No. 3,664,841; No. 3,615,606 and No. 3,849,140, and in German Offenlegungsschrift No. 2,162,899.

$\alpha$-Halocarbonyl compounds of the general formula IV are already known per se and, if not available commercially, can be obtained by the following general methods:

A. By chlorination of $\alpha$-hydroxy-ketones with thionyl chloride
B. By halogenation of keto compounds with the following halogenating agents:
 a. sulphuryl chloride,
 b. halosuccinimides such as chlorosuccinimide or bromosuccinimide or
 c. halogens such as chlorine or bromine;
C. By ester condensation, e.g. by the reaction of oxalic acid or its diethylester with ethyl chloroacetate in the presence of sodium ethylate, $\alpha$-chloro-$\beta$-keto-succinic acid ethyl ester is obtained in accordance with the following reaction scheme:

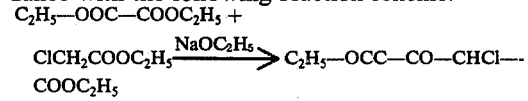

D. By Darzens condensation described by MacDonald and Schwab in J. Org. Chem. 29, 2459 (1964), in which aldehydes react with dichloroacetates in the presence of sodium methylate via an $\alpha$-chloro-epoxide stage and transposition into the $\beta$-chloro-$\alpha$-carbonyl carboxylic acid ester according to the following reaction scheme:

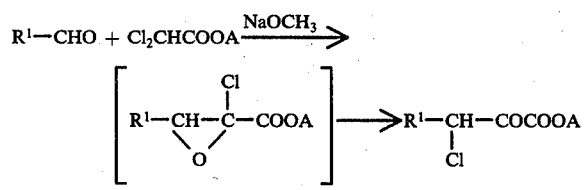

in which
A represents alkyl or aryl and
$R^1$ has the same meaning as defined for the general formula I.

Oxazolinones of the above general formulae II and III used according to the invention in which $R^2$ represents a substituted or unsubstituted amino group can be prepared by either of two basic methods. Either a suitably substituted $\alpha$-haloketone which already contains the amino group, is converted into the desired coupler compound by reaction with alkali metal cyanates, or a suitably substituted $\alpha$-halo compound of the above formula IV in which $R^1$ represents COOA and A represents alkyl or aryl is used as starting compound. These $\alpha$-halo-$\beta$-ketocarboxylic acid esters are first reacted with alkali metal cyanates to form the corresponding oxazolinone-2 compounds of the above formula II in which $R^2$ represents alkoxy or aroxy. In a second reaction stage, the resulting oxazolinone compounds of the general formula II are then converted into the desired amides.

Carbalkoxy compounds of the general formula II can be converted into the amide compounds either directly by amidation in accordance with the method of Bodroux, which has been described, for example, in Bull. soc. chim. 33, 831 (1905), using a primary or secondary amine, or by a direct aminolysis of the corresponding aryl ester in known manner, using primary or secondary amines, or the necessary amine exchange can be carried out after saponification of the alkyl or aryl ester and conversion into the corresponding acid chloride.

Amides of formula III can be formed by acid elimination of isobutene from the corresponding tertiary butyl esters followed by conversion of the resulting carboxylic acids into the corresponding acid chlorides which then in turn can be amidated.

Compounds of the above formula II in which $R^2$ represents a longer chain alkoxy group are prepared by transesterification of the corresponding methyl or ethyl esters in the presence of alkalies in known manner.

Compounds of the above formula II in which $R^2$ represents a hydroxyl group can be prepared, as already mentioned, by mild alkaline saponification of the corresponding phenyl or methyl or ethyl esters. Alternatively, the above mentioned acid elimination of isobutene from t-butyl esters may be employed for the preparation of 4-carboxyoxazolinone-2- compounds.

Compounds of the above formula III in which $R^2$ represents a hydroxyl group can easily be prepared from 5-t-butyloxy-carbonyloxazolinone-2-compounds by acid elimination of isobutene to produce the corresponding 5-carboxyoxazolinone-2- compounds.

The introduction of groups which confer diffusion resistance into the coupler molecule to be used according to the invention may be carried out by the usual methods employed in the chemistry of couplers.

For example, acylamino groups such as A-COHN-, A-O-CO-NH-, or A-NH-CO-NH-, in which A represents alkyl or aryl can be introduced into the coupler molecule by the following methods.

i. By reduction of a nitro group in the coupler molecule of the above formula I, which nitro group is substituted on a phenyl group. As example may be mentioned the catalytic hydrogenation with hydrogen on a palladium charcoal catalyst. The corresponding amino compound is then acylated by the usual methods with an acid chloride, a chloroformic acid ester or an isocyanate.

ii. By similar reduction and acylation of a nitrophenyl in a ketomethylene compound which is then halogenated by method A or B described above, and finally condensed with alkali metal cyanate to yield the corresponding oxazolinone-2 compounds containing acylamine groups.

Introduction of acylamino groups into oxazolinones-2 of the general formula II and III can also be achieved by the following additional methods:

iii. By reaction of the corresponding acid chlorides with appropriately monoacylated phenylenediamines.

iv. By aminolysis of acid chlorides with nitroaniline and reduction of the nitro group in the resulting nitroanilide by the method described above, followed by acylation.

v. By reaction of N-alkyl-acylamino-substituted or N-aryl-acylamino-substituted anilines with the corresponding carboxylic acid esters using the above-mentioned method of Bodroux.

vi. By aminolysis of keto compounds of the following formula V

R—CO—CH$_2$—R$^1$ in which $R^1$ represents COOA and R is as defined above, with monoacylated phenylene diamines. The resulting reaction product is then halogenated by method A or B described above and converted into the desired oxazolinone-2 by reaction with alkali metal cyanates.

vii. By aminolysis of keto methylene compounds of formula V with nitroanilines. The nitro group is subsequently reduced and acylated as described above. Some ketomethylene compounds will not produce the desired product, then methods iii, iv and vi are preferred.

The following methods may be employed for the introduction of solubilizing groups into the coupler molecule:

α. The amino compounds required for the acylation reactions i, ii, iv and vii described above are reacted with α-sulphopalmitic acid or o-sulphobenzoic acid anhydride. Satisfactory yields are obtained.

β. A ketomethylene compound containing a sulpho group is halogenated in the usual manner and converted to the desired oxazolinone-2 by reaction with alkali metal cyanate.

γ. Lastly, oxazolinone-2 compounds containing sulpho group are obtainable by subsequent sulphonation of compounds of the general formula I or II or III.

The preparation of coupler compounds according to the present invention is described in detail below.

Preparation 1 (Coupler 6)

1st stage 97.5 g (0.2 mol) of 2-tetradecyloxybenzolacetic acid methyl ester were dissolved in 500 ml of ethanol. 15 g of sodium hydroxide (0.375 mol) were added as a 5% aqueous solution and the reaction mixture was heated to boiling for 6 hours. The methyl alcohol formed in the reaction was for the most part evaporated off and the residue was taken up in ether. The ethereal phase obtained was purified in the usual manner by extraction with water and drying over sodium sulphate, and the ether was then removed. The residue was recrystallized from methanol. The yield was 21.6 g of 2-tetradecyloxyphenylmethylketone, having a melting point of 40° to 41° C.

2nd Stage 21.6 g of the ketone (0.065 mol) obtained in stage 1 were dissolved in 200 ml of absolute benzene. 3.3 ml (0.065 mol) of bromine dissolved in 30 ml of benzene were added dropwise at room temperature, the bromine being decolorized in the process. The solution in benzene was then purified in the usual manner by shaking with water and drying over sodium sulphate, and the benzene was removed under vacuum. The yield was 23 g of 2-tetradecyloxyphenylbromomethylketone which had a melting point of 63° to 67° C after recrystallization from methanol.

3rd stage 4.1 g of the bromine compound obtained in Stage 2 (0.01 mol), 15 ml of hexamethylphosphoric acid triamide and 2.6 g of sodium cyanate (0.04 mol) were stirred for 2 hours at 90° to 100° C. The reaction product was then poured on water and acidified with glacial acetic acid. The precipitate was filtered off, dried and recrystallized twice from butyl chloride. The yield was 0.75 g of Coupler 6, which had a melting point of 109° to 111° C.

Coupler 1 was obtained in a similar manner from chloromethylphenylketone and sodium cyanate, Coupler 2 from chloromethyl-methylketone, and Coupler 7 from α-chlorophenylacetaldehyde.

Preparation 2 (Coupler 11)

1st Stage

α-Chloro-α-phenyl-acetophenone was prepared from benzoin according to the method described in Org.Synth.Coll. Vol.II, 159.

2nd Stage 23 g (0.1 mol) of the desyl chloride prepared in Stage 1 were dissolved in 100 ml of acetonitrile and the solution was added dropwise to a suspension of 26 g (0.4 mol) of sodium cyanate in 100 ml of hexamethylphosphoric acid triamide with stirring at a bath temperature of 90° C over a period of 30 minutes. After a further reaction time of 15 minutes, the reaction mixture was introduced into 250 ml of ethyl acetate and then filtered from impurities. The solution in ethyl acetate was acidified with glacial acetic acid and shaken several times with water. The solid residue obtained after removal of the solvent under vacuum was recrystallized from glacial acetic acid.

The resulting compound 4,5-diphenyloxazolinone-2 was completely identical in its IR and NMR spectra to the compound obtainable by the methods described in the literature. It had a melting point of 207° to 209° C after it has been recrystallized once from glacial acetic acid (the melting point given in Chem. Ber. 89, 1757 (1956) is 211° C).

Preparation 3 (Coupler 12)

1st stage 4.05 g (0.03 mol) of sulphuryl chloride dissolved in 4 ml of carbon tetrachloride were added dropwise to a solution of 6.4 g (0.03 mol) of 4-fluorodesoxibenzoin and 2.5 g (0.03 mol) of sodium acetate sicc. in 80 mol of glacial acetic acid and 10 ml of carbon tetrachloride at 35° C with stirring over a period of 15 minutes. After a further reaction time of one hour, the reaction mixture was stirred into 400 ml of water, and the organic phase was taken up in carbon tetrachloride. The carbon tetrachloride phase was then separated, isolated and purified in the usual manner. After evaporation of the solvent, the residue, consisting of α-chlorobenzyl -(4-fluorophenyl)-ketone was converted, without further purification, to the final product in a similar manner to the method employed in Stage 2 of preparation 2. The resulting 4-phenyl-5-(4-fluorophenyl)-oxazolinone-2 had a melting point of 168°-171° C.

Couplers 3, 4, 5, 8, 9, 10, 13, 14, 15, 16, 17, 18, 21, 22 and 23, were prepared in a similar manner. The corresponding α-chloroketone compounds were prepared either from α-hydroxyalkyl ketones as described in preparation 2 or from dialkyl ketones as described in Preparation 3.

Preparation 3A (Coupler 19)

Coupler No. 15 is catalytically hydrogenated using a palladium/animal charcoal catalyst without application of pressure. The resulting amino compound is reacted with chloroformic acid cetyl ester by known methods, for example as described in German Patent Specification No. 1,176,479 or in German Offenlegungsschrift No. 1,797,083, to yield 5-(4-methoxyphenyl)-4-(4-cetyloxycarbonylaminophenyl)oxazolinone-2.

Preparation 4 (Coupler 27)

1st Stage 1,3-dioxo-1(2-tetradecyloxyphenyl)-butane was prepared by reacting 2-tetradecyloxybenzoic acid methyl ester and acetone in the presence of sodium ions as described by Bloch and v.Konstanecki in Ber. 33, 1998.

2nd Stage

Chlorination of the reaction product obtained in Stage 1 was carried out in accordance with Stage 1 of preparation 3. 2-Chloro-1,3-dioxo-1(2-tetradecyloxyphenyl)-butane was obtained.

3rd Stage

Reaction of the compound obtained in Stage 2 with sodium cyanate was carried out as in Stage 2 of preparation 2. 4-acetyl-5-(2-tetradecyloxyphenyl)-oxazalinone-2was obtained.

Couplers 25 and 29 were obtained in a similar manner. Couplers 24, 26, 28 and 30 are prepared from α-diketone compounds instead of β-diketone compounds.

Preparation 5 (Coupler 41)

1st Stage 119.5 g of benzoyl acetic acid ethyl ester and 53.4 g of sodium acetate sicc. were dissolved in 1 l of glacial acetic acid and 100 ml of carbon tetrachloride at 40° C. A solution of 52 ml of sulphuryl chloride (density 1.67) in 50 ml of glacial acetic acid was added dropwise with vigorous stirring at 35°-40° C over a period of one hour. The reaction mixture was then stirred for one hour at 40° C and poured on about 10 l of water. The precipitated oily product was taken up with ethyl acetate and treated in the usual manner. 124 g of α-chlorobenzoylacetic acid ethyl ester were obtained.

2Stage 22.6 g of α-chlorobenzoylacetic acid ethyl ester, 100 ml of hexamethylphosphoric acid triamide and 31 g of sodium cyanate were heated to a bath temperature of 100° C with vigorous stirring. After a reaction time of 3-½ hours, the reaction mixture was poured into about 2 l of water and acidified with glacial acetic acid. The resulting precipitate was dissolved in ethyl acetate, whereupon the organic phase was worked up in the usual manner to deposit a residue that was recrystallized from a 6:1 mixture of petroleum hydrocarbons and ethyl acetate. 12 g of 4-Ethoxycarbonyl-5-phenyl-oxazolinone-2 with a melting point of 167°-169° C were obtained Couplers 36, 37, 40, 42, 47, 51, 56 and 58 were prepared in a similar manner, using the appropriately substituted benzoyl acetic esters of the corresponding aliphatic or aromatic alcohols. Compound 58 was prepared from the correspondingly acyl substituted benzoyl acetic ester.

Preparation 6 (Coupler 55)

1st Stage

The conversion of 2-tetradecyloxybenzolacetic acid methyl ester (obtainable according to Example 1 of U.S. Pat. No. 3,849,140) to α-chloro-2-tetradecyloxybenzoyl-acetic acid methyl ester was carried out in a manner similar to that of preparation 2, stage 1.

2nd Stage 42.5 g (0.1 mol) of α-chloro-2-tetradecyloxybenzoyl acetic acid methyl ester were dissolved in 150 ml of acetonitrile and added dropwise over a period of 45 minutes, with stirring, to a suspension of 32.4 g (0.4 mol) of potassium cyanate in 120 ml of hexamethylphosphoric acid triamide at a bath temperature of 100° C. After a reaction time of 60 minutes, the reaction mixture was poured in 350 ml of ethyl acetate and filtered from unreacted potassium cyanate. Hexamethylphosphoric acid triamide was extracted by shaking the filtrate several times with water, and the ethylacetate phase was then worked up in the usual manner. After removal of the solvent under vacuum, the oily residue remaining was dissolved in a petroleum ether boiling at 50° to 55° C, and recrystallized. 29 g of 4-methoxycarbonyl-5-(2-tetradecyloxyphenyl)-oxazolinone-2with a melting point of 71° to ;b 73° C were obtained.

Couplers 38, 39, 43, 44, 46, 48, 50, 52, 53 and 59 were obtained in a similar manner.

Substantially the same results are obtained when the method of preparation 2 is employed for preparing the coupler compounds mentioned above.

Preparation 6A (Coupler 45)

This coupler was prepared by ester interchange between Coupler 41 and tetradecanol, by known methods.

Preparation 6B

Couplers 31 to 35 were obtained by saponification of the corresponding alkyl ester (e.g. couplers 36, 37, 38, 41 and 45) in 90% alcohol in the presence of 2 to 5 equivalents of potassium hydroxide.

Preparation 6C (Coupler 57)

4-Ethoxycarbonyl-5-m-nitrophenyl-oxazolinone-2(Coupler 51) is obtained by reacting α-chloro-m-nitrobenzoylacetic acid ethyl ester with potassium cyanate as in Stage 2 of preparation 6.

4-Ethoxycarbonyl-5-m-stearoylaminophenyl-oxazolinone-2 (Coupler 57) is prepared by mild catalytic hydrogenation of Coupler 51 with a palladium/animal charcoal catalyst, and acylation of the amino compound thus formed, with stearyl chloride.

Preparation 7 (Coupler 69)

4.53 g of β-Chlorophenylpyruvic acid methyl ester (prepared according to Org.Chem. 29, 2459) were dissolved in 25 ml of acetonitrile and slowly added dropwise to a suspension of 6.4 g of sodium cyanate in 30 ml of hexamethylphosphoric acid triamide at 90° C. After a reaction time of 10 minutes at 90° C, the reaction mixture was poured into water and treated in the usual manner as described above. The yield was 2.05 g of 4-phenyl-5-methoxycarbonyl-oxazolinone-2, M.p. 204°–206° C.

The yield could be increased to 2.15 g by the addition of 0,5 ml of water to the reaction mixture described above.

Substantially equally high yields were obtained when dimethylformamide or dimethylsulphoxide were used instead of the acetonitrile solvent mentioned above. The yield in the first case was 1.95 g and in the second case 1.75 g.

Couplers 60, 61, 62, 63, 66, 67, 72 to 81, 83 and 84 are prepared in a similar manner.

Preparation 7A

Coupler 64 can be obtained by the removal of isobutylene from Coupler 65 by the method described in Methoden der Org.Chemie by Houben-Weyl, Volume 8, page 420.

Preparation 8 (Coupler 70)

1st Stage 74 g of t-butylalcohol, 79 g of pyridine and 250 ml of anhydrous ether were heated to boiling and 146 g of dichloroacetyl chloride were added dropwise to the reaction mixture at such a rate that the mixture continued to boil without further supply of heat. When all the dichloroacetyl chloride has been added, boiling was continued for 3 hours. Water was then added to the reaction mixture and the ethereal phase was separated off. The resulting reaction solution was processed in the usual manner to yield 140 g of α, α-dichloroacetic acid-t-butyl ester.

2nd Stage 18.5 g of the ester obtained in Stage 1, 10.6 g of freshly distilled benzaldehyde and 70 ml of absolute ether were cooled to a temperature of between −5° C and 0° C in a mixture of ice and salt, and 13 g of solid sodium t.-butylate were added to the reaction mixture in small portions. When addition of the sodium butylate was completed, the reaction mixture was slowly warmed up to room temperature. It was then boiled under reflux for 30 minutes. After the reaction mixture had again cooled to room temperature, water was added until a clear solution was obtained. The ether layer was then separated off and washed with water until neutral in reaction. The product was then worked up in the usual manner to yield 17 g of α-oxo-β-chloro-β-phenylpropionic acid-t.-butyl ester.

3rd Stage

The reaction to the desired 4-phenyl-5-t.-butoxycarbonyl-oxazolinone-2 compounds, which have the melting point of 154° to 156° C, was carried out as described in Preparation 2, Stage 2.

Compound 65 was prepared in a similar manner but using pivalaldehyde instead of benzaldehyde.

Preparation 8A

Coupler 71 was obtained by transesterification of Compound 69 or 70 with tetradecanol.

Preparation 9 (Coupler 88)

1st Stage 19.2 g of Benzoylacetic acid ethyl ester and 87 g of morpholine were stirred for 4 hours at a bath temperature of 130° to 140° C. The excess morpholine was then distilled off and the desired reaction product consisting of benzoyl acetomorpholide was obtained as residue.

2nd Stage

The conversion of the morpholide to α-chlorobenzoylacetomorpholide was carried as described in Preparation 3, Stage 1.

3rd Stage

Conversion of the chloro compound obtained in Stage 2 into 4-morpholinocarbonyl-5-phenyloxazolinone-2 was carried out as in Stage 2 of Preparation 2 or as in Preparation 7.

Compound 98 was obtained in a similar manner.

Preparation 10 (Coupler 87)

1st Stage 44.7 g of myristoylacetic acid ethyl ester, 25.85 g of 6-chloro-3-nitroaniline and 80 ml of o-xylene were heated to 180° C with stirring on an oil bath for 3 hours, the ethyl alcohol formed being continuously distilled off. The solvent was then removed by distillation and the residue poured into 400 ml of methanol, and the resulting precipitate was filtered off. The yield was 47 g and the product had a melting point of 73° to 75° C.

2nd Stage 4.1 ml of sulphuryl chloride in 5 ml of glacial acetic acid were added dropwise at 40° C to 21.5 g of the 6-chloro-3-nitroanilide which had been prepared according to Stage 1, 100 ml of glacial acetic acid, 20 ml of carbon tetrachloride and 5 g of anhydrous sodium acetate. After 30 minutes' heating to 40° C, an additional 3 ml of sulphuryl chloride was added gradually. The progress of this reaction can be followed by thin layer chromatography in the usual manner. The reaction is completed when the thin layer chromatogram shows that chlorination has practically been completed and no starting compound can be seen to any significant extent in the reaction mixture. The product is worked up by the usual methods. The crude product obtained is recrystallized from butyl chloride. The yield was 15 g and the product had a melting point of 93° to 95° C.

3rd Stage 4.6 g of the α-chloro-6-chloro-3-nitroanilide compound obtained according to Stage 2, 20 ml of acetonitrile and 5 ml of hexamethylphosphoric acid triamide were added dropwise to a suspension of 3.5 g of sodium cyanate in 20 ml of hexamethylphosphoric acid triamide at 100° C. After a reaction time of 25 minutes at 100° C, the reaction mixture was poured into a 1:1:1 mixture of water, glacial acetic acid and ethyl acetate and treated as described in Preparation 2, Stage 2. The resulting 4-[N-(3nitro-6-chlorophenyl)-carbamoyl]-5-tridecyl-oxazalinone-2-(Coupler 87) had a melting point of 102°-104° C.

Couplers 92, 94, 96 and 100 were prepared in a similar manner, using the appropriate substituted aniline.

Preparation 11 (Coupler 95)

1st Stage

Coupler 33 was boiled in excess thionyl chloride for 60 minutes and the resulting 5-phenyl-oxazolinone-2-carboxylic acid chloride-4 was isolated in the usual manner.

2nd Stage 22.3 g of the carboxylic acid chloride obtained from Stage 1 and 31.9 g of N-methyl-o-tetradecyloxyaniline in 200 ml of acetonitrile ml were heated to boiling for 30 minutes. The desired coupler compound 95crystallized on cooling. The yield was 41 g and the product had a melting point of 41 g and the product had a melting point of 82° to 84° C.

Compounds 85, 93, 96, 99 and 102 were prepared in a similar manner.

Preparation 12 (Coupler 101)

20 g of a 3 molar solution of methyl magneisum chloride in tetrahydrofuran were diluted with 20 ml of ether and cooled to 0° C. 7.75 g of N,N-dibutylamine in 10 ml of tetrahydrofuran were added dropwise to the cooled solution over a period of 10 minutes with vigorous stirring. After a reactiom time of one hour, during which the reaction mixture was stirred at room temperature, 8.8 g of coupler compound 55 (preparation 6) dissolved in 80 ml of absolute ether were added dropwise and the mixture was then heated to boiling under reflux for one hour. After cooling to 0° C, 30 ml of an N/10 HCl solution were carefully added to the reaction mixture. The ethereal solution was then extracted with an N/2 HCl solution until neutral in reaction, dehydrated over anhydrous sodium sulphate and evaporated to dryness. After the addition of petroleum ether (boiling range 50° to 75° C) and stirring, a crystalline product consisting of 5-(2-tetradecyloxyphenyl)-oxazolinone-2-N,N-dibutyl-carbonamide-4 was obtained.

Couplers 86, 89, 90, 91, 93, 96, 97 and 99 were obtained in a similar manner by reacting Couplers 39, 41, 43, 44 and 55. Coupler 100 is similarly made from the corresponding precursor.

Preparation 13 (Coupler 107)

1st Stage

4-Phenyl-oxazolinone-2-carboxylic acid chloride-5 was prepared from coupler 68 according to Stage 1 of preparation 11.

2nd Stage 2.23 g of the carboxylic acid chloride prepared according to Stage 1 were heated to boiling under reflux for 30 minutes with 3.05 g of 2-tetradecyloxyaniline in 25 ml of acetonitrile. After cooling, the resulting white precipitate consisting of 4-phenyl-5-(2'-tetradecyloxyanilido)-oxazolinone-2was filtered off. The yield was 4.5 g and the product had a melting point of 157° to 159° C.

Couplers 104, 105, 106, 112 and 120 were prepared in a similar manner.

Preparation 14(Coupler 127)

The reaction described in preparation 12 was carried out on Coupler 69 and 4-amino-benzenesulphonic acid-N-phenyl-N-octadecylamide. The product so produced melted at 157°-159° C.

Couplers 103, 108, 111 to 117, 119, 121, 123, 128 and 130 were prepared in a similar manner from couplers 43, 50, 61, 63, 69, 72, 73, 74, 77, 78, 80, 81 and 83.

Preparation 15(Coupler 125)

1st Stage

Coupler 87 was converted into the corresponding amino compound by mild catalytic hydrogenation with hydrogen, using a palladium/animal charcoal catalyst.

2nd Stage 4.35 g of the amino compound obtained in Stage 1 were heated to boiling under reflux with 2.76 g of o-sulphobenzoic acid anhydride in 80 ml of benzene for one hour. 80 ml of acetonitrile were then added and the crystalline product obtained was filtered off. This reaction product was then purified by recrystallization from methanol followed by treatment with sodium methylate and then with glacial acetic acid. The yield was 1.45 g.

Preparation 15A

The preparation of coupler compound 125 was also achieved by conversion of the 2'-chloro-5'-nitroanilide obtained in Stage 1 of Preparation 10 into the corresponding amino compound by catalytic hydrogenation followed reaction of the amino compound with o-sulphobenzoic acid anhydride and the conversion of the resulting reaction product into the desired coupler as described in Stages 2 and 3 of Preparation 10. The analytical data clearly show that the coupler is identical with that produced by preparation 15.

Preparation 16(Coupler 129)

1st Stage p-Methoxybenzoylacetyl-(2'-cetyloxy-5'-N-methyl-sulphamyl-anilide)- was connected into the corresponding 60-chloro-substituted compound.

2nd Stage

The reaction of 23.4 g of the α-chloro compound with 13 g of sodium cyanate in a solvent mixture of 75 ml of acetonitrile and 75 ml of hexamethylphosphoric acid triamide at a bath temperature of 100° C for 15 minutes after all the reactants have been added, yielded 6.9 g of coupler 129.

Preparation 17 (Coupler 126)

0.57 g of coupler 129 were introduced portionwise as a powder into 2.5 ml of 100% sulphuric acid. The temperature rose from 20° C to 25° C. Coupler compound 129 had completely dissolved after 30 minutes stirring at room temperature. 0.27 ml of 20% oleum was then added dropwise and the mixture stirred at room temperature for a further 45 minutes. The reaction mixture was then poured into a mixture of water, ethyl acetate and concentrated hydrochloric acid. The ethyl acetate phase obtained was separated off and then worked up in the usual manner including a final wash with acetonitrile. The yield was 0.4 g.

Preparation 18

According to another method, coupler 126 was prepared by the reaction of 3.55 g of α-chloro-4-methoxy-5-sulphobenzoylacetyl-(2'-cetyloxy-5'-N-sulphamylanilide) in 15 ml of hexamethylphosphoric acid triamide and 3.5 g of sodium cyanate at 95° C for 45 minutes. The yield was 2.8 g.

The analytical data clearly show that the coupler compounds 126 prepared by the various methods described above are completely identical.

As already mentioned, the colour couplers to be used according to the present invention have an exceptionally high coupling activity. Dyes of great brilliance are obtained in color development.

Starting from normal β-ketoacetanilides and converting them into the corresponding oxazolinone-2 compounds results in color couplers which when coupled with oxidized color developer give rise to dyes which in comparison with unreacted β-ketoacetanilides are pure yellow and less orange in tone.

The effect produced according to the present invention is illustrated in the Figures, using simple coupler compounds as examples.

In FIG. 1, graph 1 is the absorption curve of the dye produced from color coupler 41 and oxidized N,N-diethyl-p-phenylene diamine developer, measured in butanol. Curve 2 is the absorption curve of a comparison dye obtained from α-chloro-benzoylacetic acid ethyl ester and oxidized N,N-diethyl-p-phenylene diamine developer. Coupler 4 can be prepared from the comparison coupler by reaction with alkali metal cyanate according to the present invention. The concentrations of the dye solutions were identical and were chosen so that an absorption corresponding approximately to a density of one was obtained. Maximum and longer wave absorption edges of the dye according to the present invention are clearly shifted towards shorter wavelengths in comparison with the αhalogen β-keto coupler compound.

FIG. 3 similarly shows the absorption curve of a dye obtained by the reaction of β-chloro-β-phenyl-pyruvic acid methyl ester with oxidized N,N-diethyl-p-phenylenediamine, measured in butanol (Curve 6) and for comparison, the absorption curve of coupler 69 (curve 5). These curves show that the comparison coupler is not suited for photograhic purposes since it gives rise to a dye which absorbs a substantial proportion of light of wavelengths above 500 mm so that an excessively reddish orange tone is produced in the yellow dye.

In FIG. 2, the absorption curve of a dye obtained by the reaction of a conventional benzoyl-2-tetradecyloxyacetanilide yellow coupler (Curve 4) with N,N-diethyl-p-phenylenediamine developer, measured in butanol, is shown for comparison beside the absorption curve of the corresponding dye obtained from coupler 107 (Curve 3). Here again it is clearly seen that the color coupler according to the invention yields a dye which absorbs at shorter wavelengths than the dye obtained from the conventional yellow coupler.

This desirable shift of the absorption appears to be an inherent effect of the cyclizing of conventional ketomethylene couplers to the oxazoline-2 structure of the present invention.

Particularly attractive colors are obtained in accordance with the present invention from benzoyl acetanilide couplers which are cyclized and do not contain a free hydrogen atom on the anilide nitrogen, for example couplers 98, 99, 95 and 89.

Color couplers which are obtained by conversion of α-keto esters into the corresponding substituted oxazolinone-2 compounds (for example coupler compounds of the structural type of formula III and those of formulae 103 to 124 and 130 to 142) couple with oxidized color developers to produce dyes which are superior in their brilliance compared with dyes obtained from conventional color couplers and satisfy all the other photographic requirements with regard to stability.

The foregoing are some of the reasons why the color couplers of the present invention are eminently suitable for use in color photographic materials.

When preparing the light-sensitive color photographic materials according to the present invention, the diffusion-resistant yellow couplers can be incorporated in known manner into the casting solutions for the silver halide emulsion layers or other colloid layers. Water-soluble couplers, that is to say couplers which contain one or more water-solubilizing groups such as sulpho or carboxyl groups (in the acid or salt form) may be incorporated as aqueous solutions whereas couplers which are not water soluble or not sufficiently soluble in water may be incorporated as solutions in suitable high boiling or low boiling organic solvents which may be either miscible or immiscible with water, or in mixtures of such solvents. The resulting solution in organic solvent is then dispersed in the aqueous colloid solution, e.g. a gelatine solution, in known manner, if desired in the presence of a wetting or dispersing agent. The aqueous hydrophilic colloid solution may, of course, also contain other additives. Water insoluble color couplers which contain fluorosulphonyl groups or carboxylic acid ester groups such as ethoxycarbonyl groups may also be converted by alkaline hydrolysis into the corresponding sulphonic acids or carboxylic acids and then used as aqueous solutions, for example in the form of their alkali metal salts.

The solution of colour coupler need not be directly dispersed or dissolved in the casting solution for the silver halide emulsion layer or some other water-permeable layer but may advantageously first be dispersed or dissolved in an aqueous, light-insensitive solution of a hydrophilic colloid, and the resulting mixture may then be carefully mixed with the casting solution of the light-sensitive silver halide emulsion layer or other water-permeable layer before it is applied, with or without first removing the organic solvents used. Suitable techniques for incorporating colour couplers in hydrophilic colloid layers of a photographic material have been described in published Dutch Patent Applications Nos. 6,516,423; 6,516,424; 6,600,098; 6,600,099 and 6,600,628; Belgian Patent 750,889; U.S. Patent 2,304,940 and British Patent Specification 791,219.

In cases where the color couplers used according to the present invention are not diffusion resistant, they can easily be added as aqueous solutions, if indicated with the addition of small quantities of aliphatic alcohols, to the usual color developer solutions conventionally used for the so-called developing-in process. For this method of development, compounds of the above formula II are preferably used.

To produce a photographic color image according to the present invention, an exposed silver halide emulsion layer is developed with an aromatic primary amino developer in the presence of a color coupler of the invention. The developers used may be any color developers capable of giving rise to azomethine dyes. Suitable developer substances include aromatic compounds such as p-phenylenediamine and its derivatives, for example N,N-dialkyl-p-phenylenediamines including N,N-diethyl-p-phenylenediamine, N,N-dialkyl-N'-sulphomethyl-p-phenylenediamines and N,N-dialkyl-N'-carboxymethyl-p-phenylenediamines.

The light-sensitive emulsions used may be emulsions of silver halides such as silver chloride, silver bromide or mixtures thereof, and may have a silver iodide content of up to 10 mol percent, in one of the conventional hydrophilic binders. The binder used for the photographic layers is preferably gelatine although it may be partly or completely replaced by other natural or synthetic binders. Suitable natural binders include, for example, alginic acid and its derivatives such as salts, esters or amides, cellulose derivatives such as carboxymethylcellulose, alkylcelluloses such as hydroxyethylcellulose, starch and its derivatives, such as ethers or esters, and carrageenates. Suitable synthetic binders include polyvinyl alcohol, partially saponified polyvinyl acetate and polyvinylpyrrolidone.

The emulsions may also be chemically sensitized, for example by the addition of sulphur compounds such as allyl isothiocyanate, allylthiourea or sodium thiosulphate at the chemical ripening stage. Reducing agents such as the tin compounds described in Belgian Pat. Nos. 493,464 and 568,687, and polyamides such as diethylene-triamine or aminomethane sulphinic acid derivatives, e.g. according to Belgian Pat. No. 547,323, may also be used as chemical sensitizers.

Noble metals such as gold, platinum, palladium, iridium, ruthenium or rhodium and their compounds are also suitable chemical sensitizers. This method of chemical sensitization has been described in the article by R. Koslowsky Z. Wiss. Phot. 46, 65 to 72 (1951).

The emulsions may also be sensitized with polyalkylene oxide derivatives, e.g. with a polyethylene oxide having a molecular weight of between 1000 and 20,000, or with condensation products of alkylene oxides and aliphatic alcohols, glycols, cyclic dehydration products of hexitols, alkyl-substituted phenols, aliphatic carboxylic acids, aliphatic amines, aliphatic diamines and amides.

The condensation products should have a molecular weight of at least 700 and preferably more than 1000. These sensitizers may, of course, be combined to produce special effects, as described in Belgian Pat. No. 537,278 and British Patent Specification 727,982.

Any emulsion that yields a subtractive yellow image must be sufficiently sensitive in the blue region of the spectrum. Non-sensitized emulsions in which the sensitivity is due to the intrinsic sensitivity of the silver halides are generally used for this purpose but the silver halide emulsions may also be sensitized in the blue spectral region, for example by means of the sensitizers described in German Offenlegungsschrift No. 1,808,041.

The emulsions of the present invention may also contain the usual stabilizers, for example homopolar or salt-like compounds of mercury which contain aromatic or heterocyclic rings, such as mercaptotriazoles, simple mercury salts, sulphonium mercury double salts and other mercury compounds. Azaindenes are also suitable stabilizers, particularly tetra- or penta-azaindenes and especially those which are substituted with hydroxyl or amino groups. compounds of this kind have been described in the article by Birr in Z. Wiss. Phot. 47, 2 to 27 (1952). Suitable stabilizers also included, among others, heterocyclic mercapto compounds such as phenylmercaptotetrazole, quaternary benzothiazole derivatives and benzotriazoles.

The emulsions of the present invention may also be hardened in the usual manner, for example with formaldehyde or halogenated aldehydes which contain a carboxyl group such as mucobromic acid, diketones, methanesulphonic acid esters and dialdehydes.

The photographic layers may also be hardened with epoxide, heterocyclic ethyleneimine or acryloyl hardeners. Examples of such hardeners have been described, for example, in German Offenlegungsschrift No. 2,263,602 and British Patent Specification 1,266,655. The layers may also be hardened by the process of German Offenlegungsschrift 2,218,009 to produce color photographic materials which are suitable for high temperature processing.

The photographic layers for color photographic multilayered materials may also be hardened with hardeners based on diazine, triazine or 1,2-dihydroquinoline as described in British Patent Specification Nos. 1,193,290; 1,251,091; 1,306,544 or 1,266,655; French Patent Specification No. 7,102,716 or German Auslegeschrift 23 32 317. Examples of such hardeners include diazine derivatives which contain alkylsulphonyl or arylsulphonyl groups, derivatives of hydrogenated diazines or triazines such as 1,3,5-hexahydrotriazine, fluorosubstituted diazine derivatives, e.g. fluoropyrimidines, esters of 2-substituted 1,2-dihydroquinoline- or 1,2-dihydroisoquinoline-N-carboxylic acids. Other suitable hardeners include vinyl sulphonic acid hardeners, carbodiimide or carbamoyl hardeners as described, for example, in German Offenlegungsschrift Nos. 2,263,602; 2,225,230 and 1,808,685; French Patent Specification No. 1,491,807; German Patent 872,153 and DDR Patent Specification No. 7218. Other suitable hardeners have been described, for example, in British Patent Specification No. 1,268,550.

The oxazolinone-2 compounds may be used according to the present invention for preparation of the usual positive, negative or reversal materials mounted on the usual support layers such as foils of cellulose triacetate, cellulose acetate, cellulose nitrate, polystyrene, polyesters such as polyethylene terephthalate, polyolefines such as polyethylene or polypropylene, baryta paper substrates or polyolefine laminated supports, e.g. polyethylene laminated paper substrates, as well as glass.

Photographic properties of the couplers of the present invention are described below with the aid of examples.

EXAMPLE 1

2 mMol of the couplers shown in the Table given below were separately dissolved, couplers 126 and 138 as alkali salts in an aqueous alcoholic solution the other couplers each in 3 ml of ethyl acetate, and separately emulsified in 20 ml of a 5 % gelatin solution at 60° C in known manner after the addition of 0.5 g of dibutylphthalate which was however not used in the emulsions containing couplers 126 and 138. The gelatine solution contained 0.16 g of the sodium salt of dodecylbenzene sulphonic acid. The resulting emulsions were then separately mixed with 85 g of a 7.5% gelatine solution in which 1.9 g of silver bromide was dispersed, and the mixtures diluted to the required casting viscosity with water. The diluted mixtures were then cast on transparent support layers of cellulose triacetate and dried. The materials obtained in this way were exposed behind a grey step wedge, developed for 8 minutes at room temperature in a conventional color developer containing the indicated developer substance, and then bleached and fixed in the usual manner.

Developer $E_1$: N,N-Diethyl-p-phenylenediamine
Developer $E_2$: N,N-Diethyl-3-methyl-p-phenylenediamine
Developer $E_3$: N-butyl-N-Δ-sulphobutyl-p-phenylenediamine Yellow step wedges with brilliant yellow dyes were obtained. Their absorption maxima are given in the Table.

Table

| Coupler | Absorption maximum | | |
|---|---|---|---|
| | $E_1$ | $E_2$ | $E_3$ |
| 6 | 447 | | |
| 27 | | 411 | |
| 55 | | | 420 |
| 95 | 422 | 430 | |
| 98 | | | 425 |
| 101 | 422 | 428 | 433 |
| 105 | 425 | 438 | 433 |
| 107 | 425 | | |
| 126 | 433 | | |
| 127 | | | 442 |
| 130 | 417 | | |
| 131 | 440 | 448 | 438 |
| 133 | 425 | 436 | |
| 135 | 426 | 440 | 433 |
| 138 | 418 | 429 | |
| 140 | 432 | 437 | 432 |
| 142 | 435 | 442 | 435 |

EXAMPLE 2

A color photographic material containing Coupler 128 was prepared as described in Example 1.

The photographic material was then divided into three portions A, B and C. Sample A was exposed behind a grey step wedge and then subjected to a conventional color negative process in which it was developed with developer $E_3$ for 8 minutes at room temperature.

Sample B was developed by a color reversal process after exposure behind the same grey step wedge. The color reversal process comprised three steps: Black-and-white development, diffuse second exposure and color development with a color developer containing the developer N-ethyl-N-β-oxyethyl-3-methyl-p-phenylenediamine. This developement was carried out for about 12 minutes at 20° C.

Sample C was subjected to a conventional instant hardening process with the carbodiimide instant hardener $C_2H_5-N=C=N(CH_2)_3-N-(CH_3)_2$. HCl before it was processed. It was then also exposed behind the same grey step wedge before it was subjected to a color negative process using the color developer for sample B. The development time was 6.5 minutes and the temperature 30° C.

Brilliant yellow step wedges were obtained for all three samples. Their absorption maxima were 455 (a); 460 (B) and 460 (C).

Similar samples containing a compound of the following formula

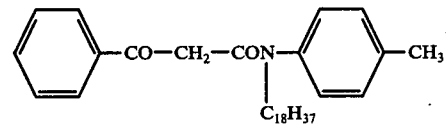

instead of the coupler of the present invention were prepared for comparison.

In each case the samples with the keto methylene coupler had a maximum light absorption at wavelengths higher than those provided in accordance with the present invention.

When the stability of the dyes obtained according to the present invention, are compared with those of dyes obtained from known couplers, it is found that the dyes according to the present invention have about the same stability to light (Xenon light and daylight) and to storage in hot air or moist warm air.

Obviously many modifications and variations of the present invention are possible in the light of the above teachings. It is therefore to be understood that within the scope of the appended claims the invention may be practiced otherwise than as specifically described.

We claim:
1. In a photographic material containing at least one silver halide emulsion layer and a photographic coupler, the improvement according to which the photographic coupler is a monocyclic-1,3-oxazolinone-2-coupling color coupler having the tautomeric

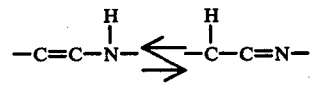

structure.
2. The improved photographic material of claim 1 in which the photographic coupler is a coupler that forms a yellow dye on becoming coupled with the oxidation product of a primary-amine-containing aromatic silver halide developer.

3. The improved photographic material of claim 1 in which the color coupler has the formula

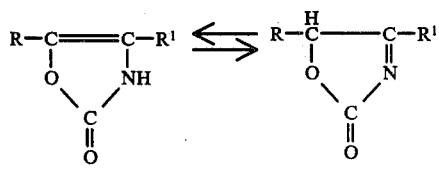

where

R and R¹ may be the same or different and represent hydrogen, alkyl, cycloalkyl, aryl, a heterocyclic group, or $COR^2$, $R^2$ standing for hydroxyl, alkoxy, aroxy, alkyl, aryl, a heterocyclic group, or an amino group which may be monosubstituted or disubstituted by alkyl, aryl or heterocyclic groups and in the case of a disubstituted amino the substituents may complete a 5- or 6-membered heterocyclic ring, and not more than one of R and R¹ is hydrogen.

4. The improved photographic material of claim 1 in which the color coupler has the formula

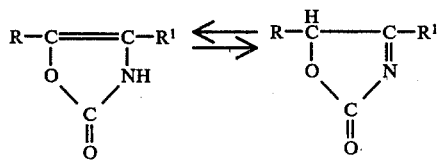

where

R and R¹ may be the same or different and represent alkyl, cycloalkyl, aryl, a heterocyclic group, or $COR^2$, $R^2$ standing for hydroxyl, alkoxy, aroxy, alkyl, aryl, a heterocyclic group, or an amino group which may be monosubstituted or disubstituted by alkyl, aryl or heterocyclic groups and in the case of a disubstituted amino the substituents may complete a 5- or 6-membered heterocyclic ring.

5. The improved photographic of claim 4 in which at least one of R and R¹ is $COR^2$.

6. The improved photographic material of claim 3 wherein one of R and R¹ is $COR^2$, the coupler also contains a diffusion-resisting substituent, and the coupler is incorporated in diffusionfast form in a layer of the photographic material.

7. The improved photographic material of claim 6 wherein the coupler is incorporated in a silver halide emulsion layer.

8. The improved photographic material of claim 2 in which the coupler is selected from the class consisting of couplers 1 through 142.

9. In the process for the production of photographic images by exposure and development of a light-sensitive photographic material containing at least one light-sensitive silver halide emulsion layer with an aromatic colour developer compound containing primary amino groups in the presence of a colour coupler that has a structural coupling moiety to which the oxidation product of a silver halide color developer couples to form a coupling product, the improvement according to which the color coupler is a monocyclic-1,3-oxazolinone-2-coupling color coupler having the tautomeric

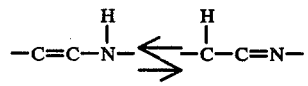

structure.

* * * * *